(12) United States Patent
Ko et al.

(10) Patent No.: US 9,763,595 B2
(45) Date of Patent: Sep. 19, 2017

(54) APPARATUS AND METHOD OF MEASURING BIO IMPEDANCE

(71) Applicants: Samsung Electronics Co., Ltd., Suwon-si (KR); The Industry & Academic Cooperation in Chungnam National University (IAC), Daejeon (KR)

(72) Inventors: Hyoung Ho Ko, Daejeon (KR); Jong Pal Kim, Seoul (KR); Tak Hyung Lee, Suwon-si (KR)

(73) Assignees: Samsung Electronics Co., Ltd., Suwon-si (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 214 days.

(21) Appl. No.: 14/600,670

(22) Filed: Jan. 20, 2015

(65) Prior Publication Data

US 2015/0201861 A1    Jul. 23, 2015

(30) Foreign Application Priority Data

Jan. 21, 2014    (KR) ........................ 10-2014-0007377

(51) Int. Cl.
```
A61B 5/00     (2006.01)
A61B 5/053    (2006.01)
A61B 5/08     (2006.01)
A61B 5/026    (2006.01)
```
(52) U.S. Cl.
CPC ............ *A61B 5/0531* (2013.01); *A61B 5/026* (2013.01); *A61B 5/053* (2013.01); *A61B 5/0537* (2013.01); *A61B 5/0809* (2013.01); *A61B 5/7228* (2013.01)

(58) Field of Classification Search
CPC ..... A61B 5/053; A61B 5/0531; A61B 5/0537; A61B 5/026; A61B 5/0809; A61B 5/7228
See application file for complete search history.

(56) References Cited

U.S. PATENT DOCUMENTS

| | | |
|---|---|---|
| 4,165,749 A | 8/1979 | Cansell |
| 5,206,602 A | 4/1993 | Baumgartner et al. |
| 5,382,956 A | 1/1995 | Baumgartner et al. |
| 5,631,555 A | 5/1997 | Takahashi et al. |

(Continued)

FOREIGN PATENT DOCUMENTS

| | | |
|---|---|---|
| DE | 10 2011 002 413 A1 | 7/2012 |
| EP | 1 786 322 B1 | 10/2009 |

(Continued)

OTHER PUBLICATIONS

Bentham, "225 Lock-in Amplifier," Bentham Instruments Ltd., Sep. 5, 2011 (12 Pages).

(Continued)

*Primary Examiner* — Max Hindenburg
(74) *Attorney, Agent, or Firm* — NSIP Law

(57) ABSTRACT

A bio impedance measurement apparatus includes a current applicator configured to provide, to terminals contacting a body, a current based on a first control signal, and a modulator configured to modulate a voltage generated as the current flows through the body, based on a second control signal. The apparatus further includes an amplifier configured to amplify the modulated voltage, and a demodulator configured to demodulate the amplified voltage based on a third control signal.

20 Claims, 18 Drawing Sheets

(56) References Cited

U.S. PATENT DOCUMENTS

| | | |
|---|---|---|
| 7,161,362 B2 | 1/2007 | Shambroom et al. |
| 7,714,757 B2 | 5/2010 | Denison et al. |
| 8,241,222 B2 | 8/2012 | Zielinski et al. |
| 2001/0051774 A1 | 12/2001 | Littrup et al. |
| 2002/0033989 A1 | 3/2002 | Fisher et al. |
| 2007/0043303 A1 | 2/2007 | Osypka et al. |
| 2007/0227253 A1 | 10/2007 | Kleven |
| 2011/0193633 A1 | 8/2011 | Yoon et al. |
| 2013/0006136 A1 | 1/2013 | Biancolillo et al. |

FOREIGN PATENT DOCUMENTS

| | | |
|---|---|---|
| EP | 2 294 979 A1 | 3/2011 |
| EP | 2 294 979 A8 | 9/2011 |
| JP | 2672327 B2 | 11/1997 |
| JP | 2013-128716 A | 7/2013 |
| JP | 2013-132326 A | 7/2013 |
| KR | 10-2007-0044825 A | 4/2007 |
| KR | 10-0707984 B1 | 4/2007 |
| KR | 10-2009-0104903 A | 10/2009 |
| KR | 10-2012-0068430 A | 10/2009 |
| KR | 10-1056016 B1 | 8/2011 |
| KR | 10-1101118 B1 | 1/2012 |
| KR | 10-1114720 B1 | 3/2012 |
| KR | 10-1114674 B1 | 5/2012 |
| KR | 10-2013-0091195 A | 8/2013 |

OTHER PUBLICATIONS

Kirby D., [time-nuts] Phase noise with a lock-in amplifier, availavle at https://www.febco.com/pipermail/time-nuts/2003-April/010873.html, Apr. 16, 2005 (4 Pages).

Extended European Search report issued on May 29, 2015 in counterpart European Application No. 15151780.2 (9 pages).

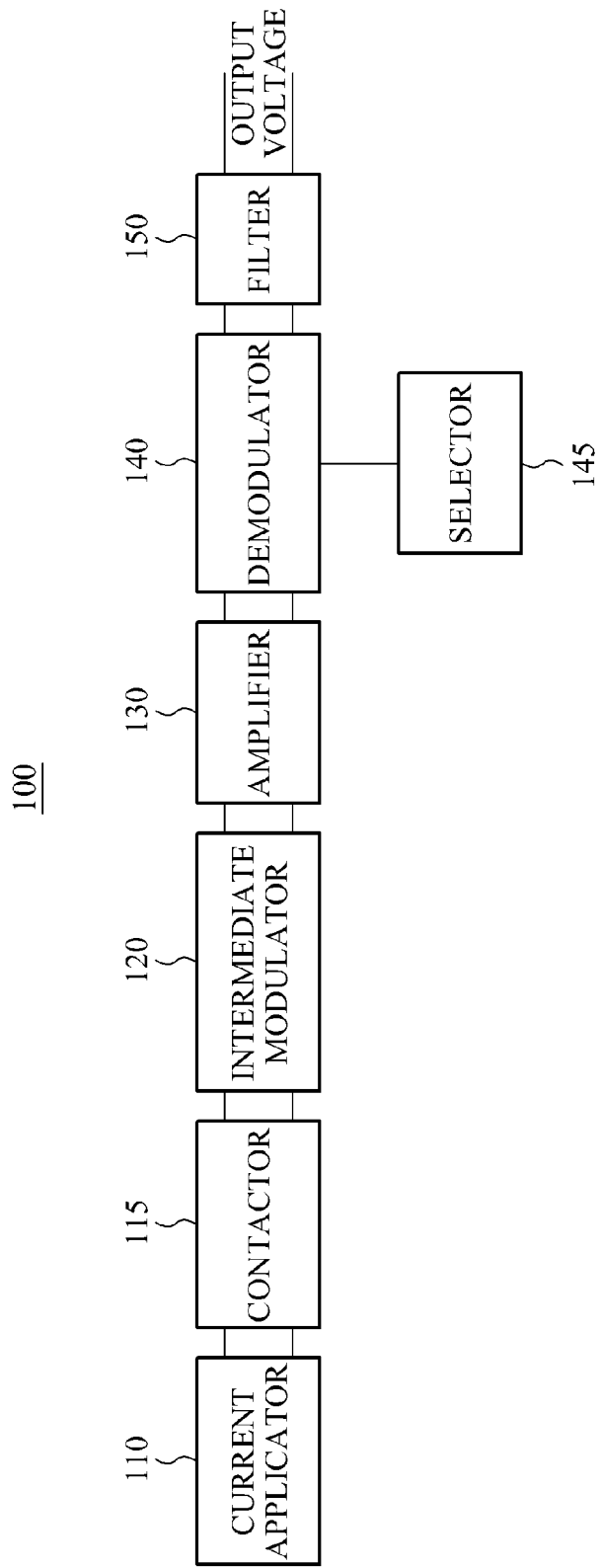

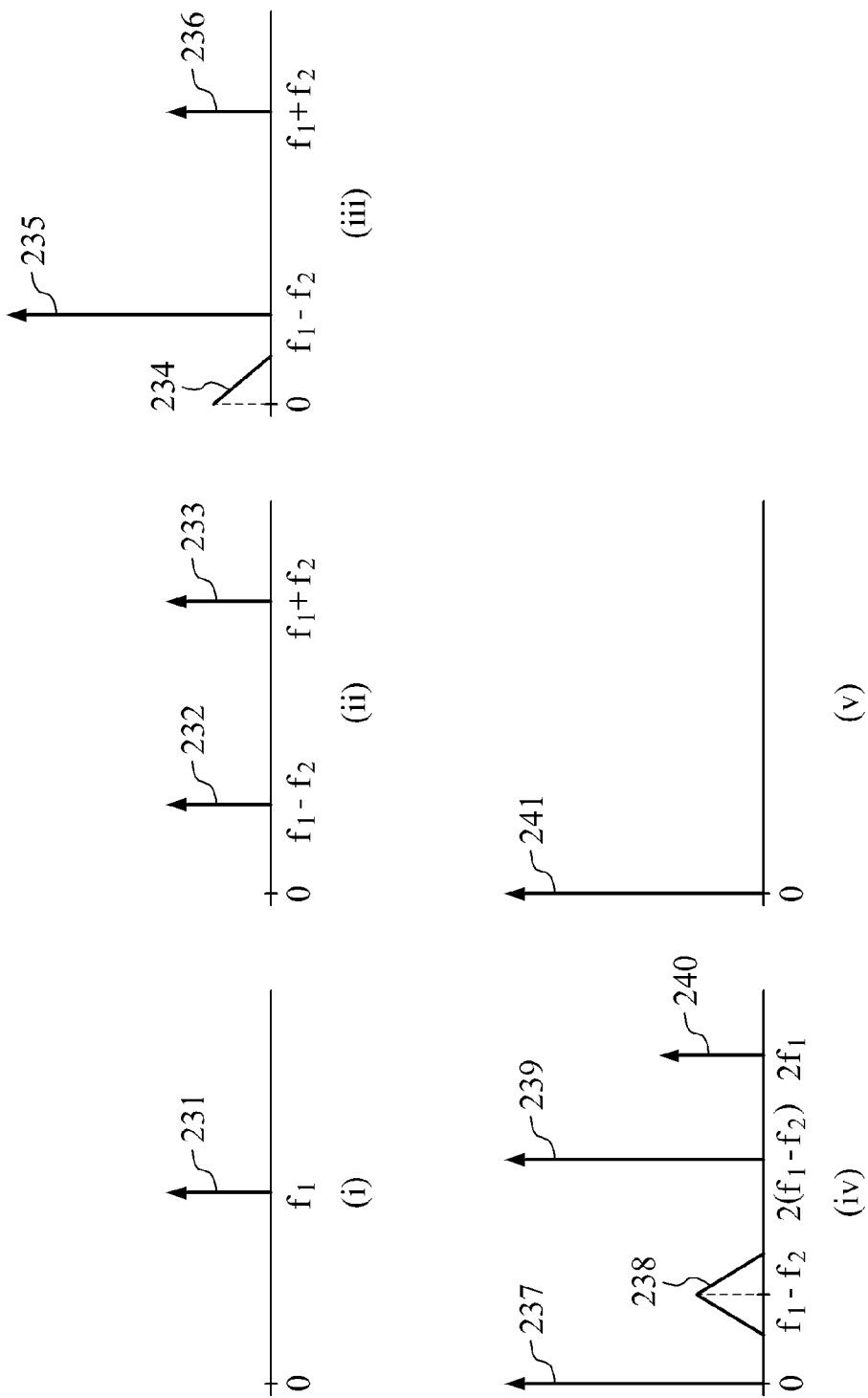

300

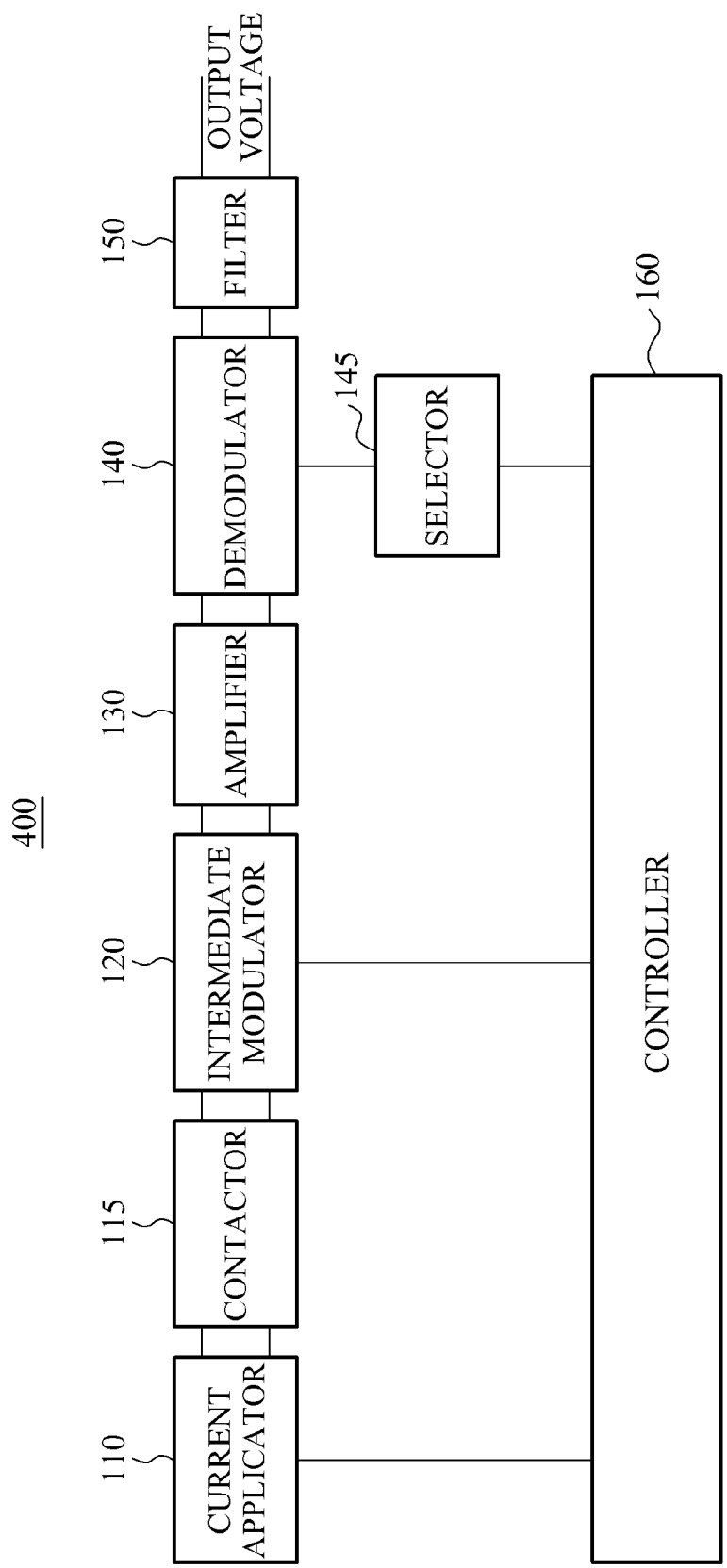

500

700

700

APPARATUS AND METHOD OF MEASURING BIO IMPEDANCE

CROSS-REFERENCE TO RELATED APPLICATION

This application claims the benefit under 35 USC 119(a) of Korean Patent Application No. 10-2014-0007377, filed on Jan. 21, 2014, in the Korean Intellectual Property Office, the entire disclosure of which is incorporated herein by reference for all purposes.

BACKGROUND

1. Field

The following description relates to an apparatus and a method of measuring bio impedance.

2. Description of Related Art

Various medical equipments for diagnosing health conditions of patients are being developed. For convenience of a patient during a health examination and for a quick result of the health examination, importance of the medical equipments for measuring electrical bio signals of patients is rising. Bio impedance may be used to monitor a health condition or an emotional condition of a living body.

SUMMARY

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter.

In one general aspect, there is provided a bio impedance measurement apparatus including a current applicator configured to provide, to terminals contacting a body, a current based on a first control signal, and a modulator configured to modulate a voltage generated as the current flows through the body, based on a second control signal. The apparatus further includes an amplifier configured to amplify the modulated voltage, and a demodulator configured to demodulate the amplified voltage based on a third control signal.

The third control signal may have a third frequency that is a difference between a first frequency of the first control signal and a second frequency of the second control signal.

The third control signal may have a third frequency that is determined based on a bandwidth of the amplifier.

The second control signal may have a second frequency that is determined so that a frequency obtained by subtracting the second frequency from a first frequency of the first control signal is in a bandwidth of the amplifier.

The first control signal may be determined based on a characteristic of a bio impedance to be measured.

The amplifier may be configured to amplify a signal generated based on the second control signal determined based on the first control signal and the third control signal.

The modulator may be configured to generate a first intermediate signal of a frequency obtained by adding a second frequency of the second control signal to a first frequency of the first control signal, and a second intermediate signal of a frequency obtained by subtracting the second frequency from the first frequency. The amplifier may be configured to selectively amplify the second intermediate signal between the first intermediate signal and the second intermediate signal.

The bio impedance measurement apparatus may further include a selector configured to select the third control signal to be a fourth control signal or a fifth control signal, the fourth control signal and the fifth control signal having different phases.

The selector may be configured to select the fourth control signal to measure a real component of a bio impedance, and select the fifth control signal to measure an imaginary component of a bio impedance.

The selector may be configured to alternately select the fourth control signal and the fifth control signal at a predetermined period.

The bio impedance measurement apparatus may further include the terminals configured to contact the body so that the current flows through the body.

In another general aspect, there is provided a bio impedance measurement method including providing, to terminals contacting a body, a current based on a first control signal, and modulating a voltage generated as the current flows through the body, based on a second control signal. The method further includes amplifying the modulated voltage, and demodulating the amplified voltage based on a third control signal.

The bio impedance measurement method may further include determining the first control signal based on a characteristic of a bio impedance to be measured, determining the third control signal based on a bandwidth of an amplifier, and determining the second control signal based on the first control signal and the third control signal.

The determining of the second control signal may include determining a second frequency of the second control signal to be a difference between a first frequency of the first control signal and a third frequency of the third control signal.

The determining of the third control signal may include determining a third frequency of the third control signal so that the third frequency is in the bandwidth of the amplifier.

The modulating may include generating a first intermediate signal of a frequency obtained by adding a second frequency of the second control signal to a first frequency of the first control signal, and a second intermediate signal of a frequency obtained by subtracting the second frequency from the first frequency. The amplifying may include selectively amplifying the second intermediate signal between the first intermediate signal and the second intermediate signal.

The demodulating may include selecting the third control signal to be a fourth control signal or a fifth control signal, the fourth control signal and the fifth control signal having different phases.

The selecting may include selecting the fourth control signal to measure a real component of a bio impedance, and selecting the fifth control signal to measure an imaginary component of a bio impedance.

The selecting may include alternately selecting the fourth control signal and the fifth control signal at a predetermined period.

A non-transitory computer-readable storage medium may store a program including instructions to cause a computer to perform the method.

Other features and aspects will be apparent from the following detailed description, the drawings, and the claims.

BRIEF DESCRIPTION OF THE DRAWINGS

FIGS. 1A to 1D are diagrams illustrating examples of a bio impedance measurement apparatus.

FIGS. 2A to 2D are graphs illustrating an example of a reduction in a bandwidth needed for an amplifier.

FIG. 4 is a block diagram illustrating an example of a bio impedance measurement apparatus further including a controller.

Figure 1B:
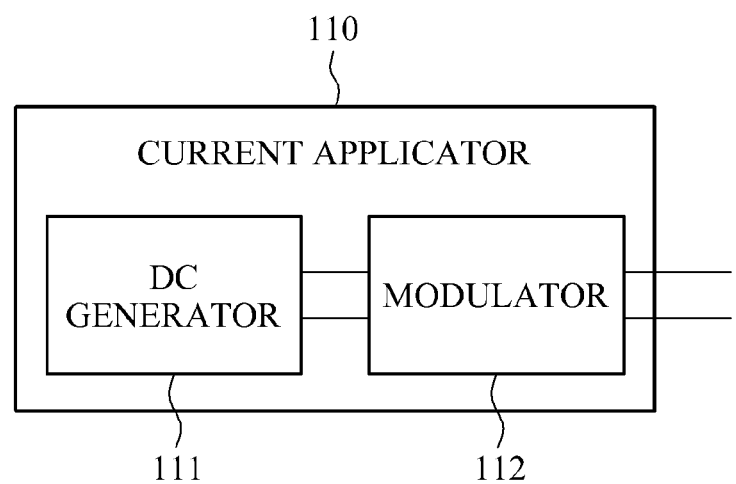

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIGS. 1A to 1D are diagrams illustrating examples of a bio impedance measurement apparatus 100. Referring to FIG. 1A, the bio impedance measurement apparatus 100 measures bio impedance. The bio impedance may be used to monitor a health condition or an emotional condition of a living body. The bio impedance may be in various types. For example, the bio impedance may include bio impedance indicating a skin resistance, bio impedance indicating a skin hydration, bio impedance changed depending on respiration by lungs, bio impedance changed depending on a blood current, and bio impedance present on an electrical path including skin and a measurement electrode.

The bio impedance measurement apparatus 100 may be applied to analysis of impedance components of a human body, such as body fat, and electrode impedance monitoring during bio signal detection such as electrocardiogram (ECG), electromyogram (EMG), electrooculogram (EOG), and brainwave. The importance of bio signal measurement is also increasing in a mobile environment, for example, ubiquitous health care. The bio impedance measurement apparatus 100 may be applied to various fields, for example, detecting bio signals such as body fat through measurement of the bio impedance in the mobile environment and monitoring respiration through impedance measurement of an electrode for bio signal detection.

To measure the bio impedance, a current generated at an outside of a body may be used. For example, bioelectrical impedance analysis may be performed based on a principle that a resistance of a uniform conductor having a predetermined length with a uniform cross sectional area is proportional to the length and inversely proportional to the cross sectional area. However, a living body is generally not a uniform cylinder, and conductivity of the living body is also not uniform along the living body. The living body is constituted by muscle and extracellular fluid having a relatively high conductivity, and fat tissue that is not electrically conductive. Therefore, various circuit models may be applied to explain electrical characteristics of a body.

When an alternating current (AC) is flown through the body, the AC passes through a cell membrane, and the cell membrane may be charged with electric charges. In this case, the cell membrane may function as a capacitor, through which the electrical characteristics of the body may be modeled. In addition, electrical transmittance of a cell may be varied according to frequencies of the AC. For example, an AC of about 5 kHz does not pass through the cell membrane, and therefore may be used for measure of the extracellular fluid. An AC of about 100 kHz or higher that passes through the cell membrane may be used for measurement of a total body water (TBW).

The bio impedance measurement apparatus 100 includes a current applicator 110. The current applicator 110 outputs an AC of a first frequency. The current applicator 110 that outputs the AC of the first frequency may be configured in various types. For example, the current applicator 110 may include a sine wave current generator. In this case, the sine wave current generator may output a sine wave current of the first frequency. As another example, referring to FIG. 1B, the current applicator 110 includes a direct current (DC) generator 111 and a modulator 112. The DC generator 111 generates a DC. The modulator 112 outputs an AC by switching an output direction of the DC generated by the DC generator 111. The modulator 112 may modulate the DC into the AC by switching the output direction of the DC, using the first frequency.

The current applicator 110 may use the first frequency corresponding to a type of bio impedance to be measured. The type of bio impedance may relate to a frequency of an AC injected into a living body for measurement of the bio impedance of the corresponding type. This is because different types of bio impedance may be measured depending on the frequency of the AC injected to the living body. The current applicator 110 may use various frequency bands such as 1 kHz, 5 kHz, 50 kHz, 250 kHz, 500 kHz, 1 MHz, and other frequencies as the first frequency to measure various types of the bio impedance.

For example, the bio impedance measurement apparatus 100 may measure various types of the bio impedance from various parts of the living body. For example, the bio impedance measurement apparatus 100 may measure bio impedances of various body parts such as a right arm, a left arm, a trunk, a right leg, and a left leg, using the various frequency bands. The measured bio impedances may be used for calculating a body weight, TBW, intracellular water, extracellular water, protein, mineral matter, muscle mass, lean body mass (LBM), skeletal muscle mass, fat mass, abdominal fat ratio, visceral fat area, muscle mass in each segment, muscle percentage in each segment, edema index (EI), and other parameters known to one of ordinary skill in the art.

When the modulated current is supplied to a bio impedance measured portion, a voltage drop may be caused due to a bio impedance of the bio impedance measured portion. The bio impedance measurement apparatus 100 may measure the bio impedance by measuring a potential difference according to the voltage drop.

Referring again to FIG. 1A, the bio impedance measurement apparatus 100 further includes a contactor 115. The contactor 115 provides a plurality of terminals for contacting the living body so that the AC output by the current applicator 110 flows through the living body.

Figure 1C:
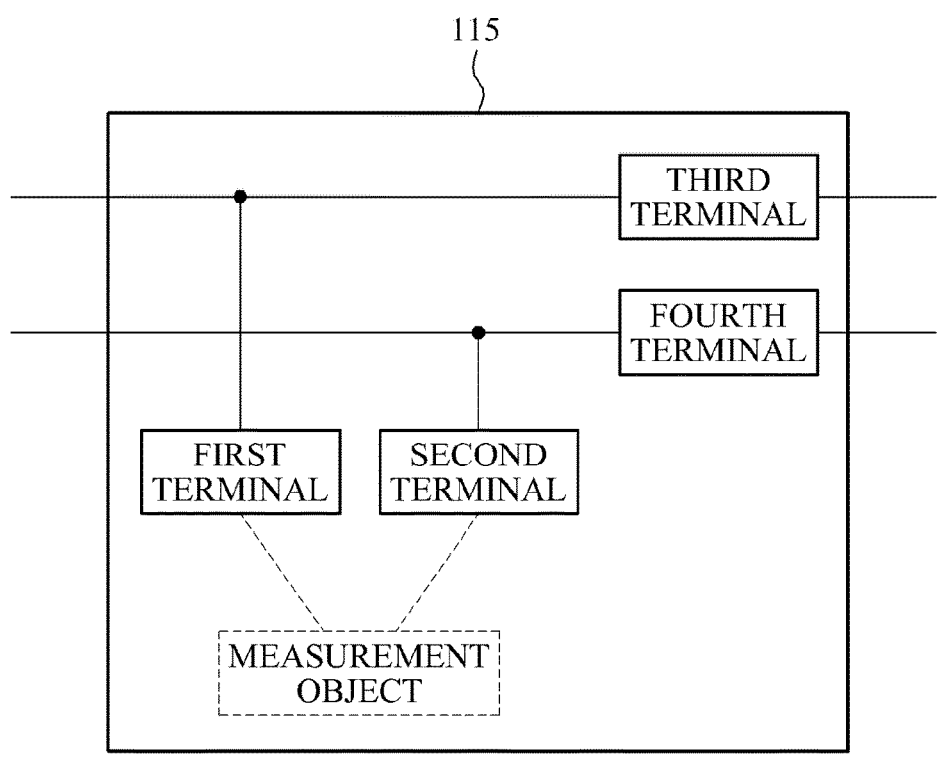

Referring to FIG. 1C, first and second terminals included in the contactor 115 are interfaced with a measurement object according to a 2-terminal measurement method. In this case, an AC is supplied to the measurement object such as the living body through the first and second terminals. As the AC flows through the living body, a potential difference is generated between the first terminal and the second terminal. The contactor 115 outputs the potential difference between the first terminal and the second terminal through third and fourth terminals, respectively.

Figure 1D:
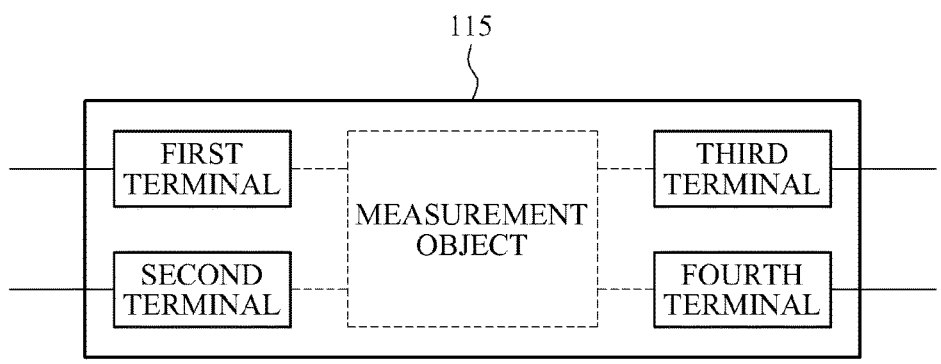

As another example, referring to FIG. 1D, first through fourth terminals included in the contactor 115 are interfaced with a measurement object according to a 4-terminal measurement method. In this case, an AC is supplied to the measurement object such as the living body through the first and second terminals, and a potential difference between the third and fourth terminals is output. A measurement result of the 4-terminal measurement method may be more precise in comparison to a measurement result of the 2-terminal measurement method.

Hereinafter, a potential difference generated between two terminals of the contactor 115 may be referred to as a voltage generated between the two terminals. Since a current flowing through the living body may be an AC output by the current applicator 110, having the first frequency as a central frequency, the voltage generated between the two terminals of the contactor 115 may be the AC having the first frequency as the central frequency.

The bio impedance measurement apparatus 100 further includes an amplifier 130. The amplifier 130 amplifies the voltage generated between the two terminals of the contactor 115 to measure the bio impedance. The amplifier 130 may include an instrumentation amplifier (IA). The IA may perform amplification and filtering of micro bio signals.

A bandwidth of the amplifier 130 may have to include the first frequency. That is, the amplifier 130 may need to sufficiently amplify a signal of the first frequency used by the current applicator 110 to correctly measure the bio impedance to be measured.

Figure 2A:
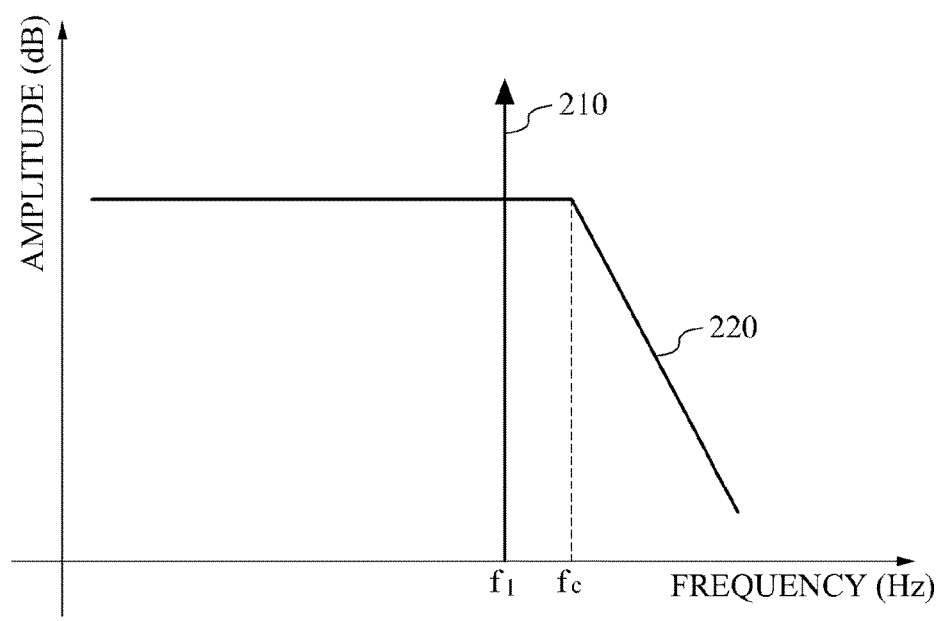

For example, referring to FIG. 2A, a cutoff frequency $f_c$ from which a frequency reaction curve 220 of the amplifier 130 starts decreasing in amplitude needs to be higher than a first frequency $f_1$ 210 used in the current applicator 110. In FIG. 2A, an x-axis denotes a frequency of a signal input to the amplifier 130, and a y-axis denotes an amplitude of a signal output from the amplifier 130. In FIG. 2A, a bandwidth of the amplifier 130 may be a frequency band less than or equal to the cutoff frequency $f_c$.

Generally, as the bandwidth of the amplifier 130 includes a high frequency band, power consumption of the amplifier 130 increases. Therefore, when a requirement specification of the amplifier 130 is reduced, power consumption of the bio impedance measurement apparatus 100 may be reduced. The bio impedance measurement apparatus 100 according to an example may provide a technology of reducing power consumption needed for measuring the same bio impedance compared to other bio impedance measurement technologies.

Referring again to FIG. 1A, the bio impedance measurement apparatus 100 further includes an intermediate modulator 120. The intermediate modulator 120 modulates the voltage generated between the two terminals of the contactor 115, using a second frequency. The voltage generated between the two terminals may be an AC having the first frequency as the central frequency. The intermediate modulator 120 may be input with the AC having the first frequency as the central frequency, and modulate the input AC into an AC having a frequency lower than the first frequency as the central frequency. The intermediate modulator 120 may reduce the needed bandwidth of the amplifier 130 by reducing the frequency of the input AC, accordingly reducing the power consumption needed for operation of the amplifier 130.

Figure 2B:
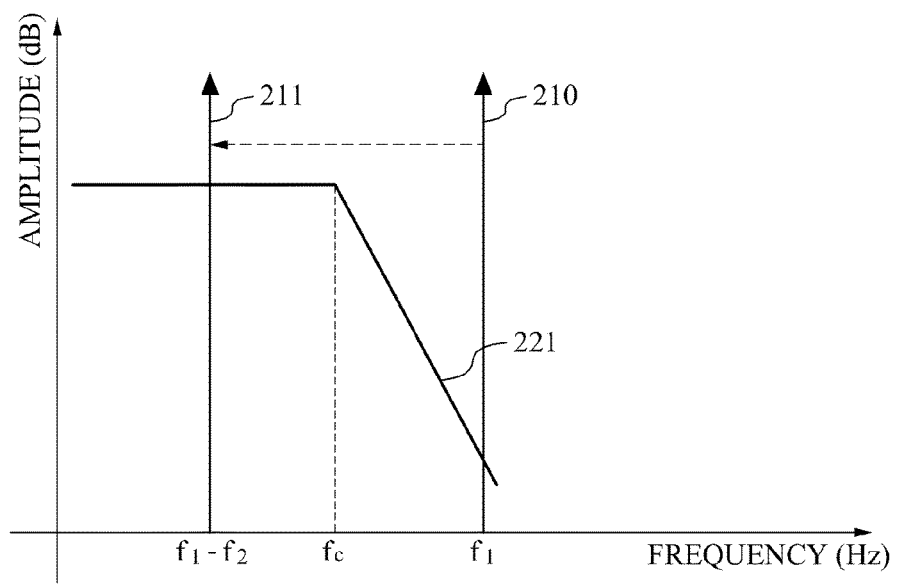

For example, referring to FIG. 2B, the intermediate modulator 120 changes the central frequency of the input signal from the first frequency $f_1$ 210 to a frequency $f_1-f_2$ 211. In this case, since the signal input to the amplifier 130 has the frequency $f_1-f_2$ 211 as the central frequency, the bandwidth of the amplifier 130 covers up to a band corresponding to the frequency $f_1-f_2$ 211 rather than a band corresponding to the first frequency $f_1$ 210. That is, a cutoff frequency $f_c$ from which a frequency reaction curve 221 of the amplifier 130 starts decreasing needs to be higher than the frequency $f_1-f_2$ 211, but is lower than the first frequency $f_1$ 210.

Figure 2C:
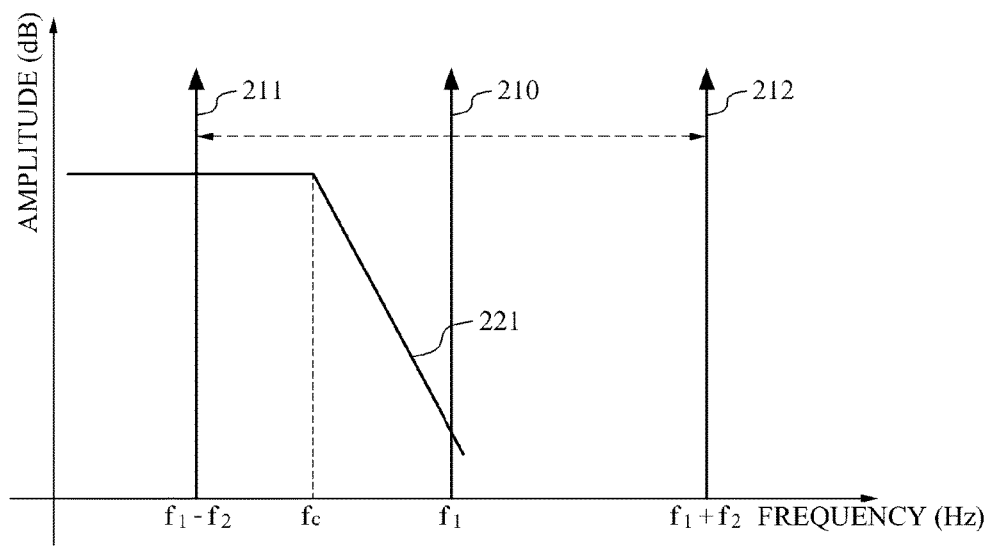

For example, referring to FIG. 2C, when the intermediate modulator 120 modulates the input signal, using the second frequency $f_2$, a signal of a frequency $f_1+f_2$ 212 may also be generated in addition to a signal of the frequency $f_1-f_2$ 211. As will be described in detail below, the bandwidth of the amplifier 130 may include only the band corresponding to the frequency $f_1-f_2$ 211 instead of being required to include the band corresponding to the first frequency $f_1$ 210 or a band corresponding to the frequency $f_1+f_2$ 212. That is, the amplifier 130 may amplify only the band corresponding to the frequency $f_1-f_2$ 211, not the band corresponding to the first frequency $f_1$ 210 or the frequency $f_1+f_2$ 212.

Referring again to FIG. 1A, the bio impedance measurement apparatus 100 further includes a demodulator 140. The demodulator 140 demodulates an output signal of the amplifier 130, using a third frequency $f_3$. The third frequency $f_3$ relates to the first frequency $f_1$ used in the current applicator 110 and the second frequency $f_2$ used in the intermediate modulator 120. For example, the third frequency $f_3$ may be a frequency that is a difference between the first frequency $f_1$ and the second frequency $f_2$. Hereinafter, the third frequency $f_3$ may be referred to as a demodulation frequency.

The bio impedance measurement apparatus 100 further includes a selector 145. The bio impedance may include a real component and an imaginary component. The selector 145 selects any one of different phase signals, and provides the selected phase signal to the demodulator 140 so that the real component and the imaginary component of the bio impedance may be selectively measured.

For example, for detection of the bio impedance, a quadrature demodulation method may be applied in a demodulation step of a chopper stabilization method. Therefore, the real component and the imaginary component of the bio impedance may be separated. Through the real component and the imaginary component, components of a human body, such as fat and moisture, may be separately analyzed. Thus, the bio impedance measurement apparatus 100 may be applied to various application fields such as body fat analysis. A detailed description about the selector 145 will be made hereinafter.

The bio impedance measurement apparatus 100 further includes a filter 150. The filter 150 may include a low pass filter (LPF) that passes signals (i.e., output voltage signals) of only a predetermined frequency or lower while interrupting signals of a frequency higher than the predetermined frequency. For example, the predetermined frequency may be the third frequency used in the demodulator 140.

Hereinafter, output signals of each module illustrated in FIG. 1A will be described in detail with reference to FIG. 2D. A graph (i) of FIG. 2D represents a voltage generated as an AC output by the current applicator 110 flows through a living body. A central frequency of a signal 231 is the first frequency $f_1$.

A graph (ii) of FIG. 2D represents a voltage modulated by the intermediate modulator 120. The intermediate modulator 120 generates a signal 232 and a signal 233 by modulating the signal 231, using the second frequency $f_2$. A central frequency of the signal 232 is the frequency $f_1-f_2$, and a central frequency of the signal 233 is the frequency $f_1+f_2$.

A graph (iii) of FIG. 2D represents a voltage amplified by the amplifier 130. The amplifier 130 amplifies only the signal 232 that is slower between the signal 232 and the signal 233, but does not amplify the signal 233 that is faster. Alternatively, a bandwidth of the amplifier 130 may include only a band corresponding to the central frequency of the signal 232 but not a band corresponding to the central frequency of the signal 233. A signal 235 is the signal 232 amplified by the amplifier 130. A signal 236 is substantially the same as the signal 233.

A signal 234 is a noise generated by the operation of the amplifier 130. For example, a 1/f noise may be generated inside the amplifier 130. The 1/f noise may be called a flicker noise, which is a unique noise generated in an active device. When the noise generated in the active device is expressed by a frequency axis, the noise may greatly increase in a low frequency band, for example, approximately 100 Hz or lower. That is, the 1/f noise may increase in inverse proportion to the frequency.

The second frequency $f_2$ is determined such that the frequency $f_1-f_2$ of the voltage modulated by the intermediate modulator 120 is not included in a noise band generated in the amplifier 130. For example, the second frequency $f_2$ is determined so that the frequency $f_1-f_2$ of the signal 235 is located out of the band of the signal 234. In this case, the measurement result of the bio impedance measurement apparatus 100 may not be interfered with the noise generated in the amplifier 130.

A graph (iv) of FIG. 2D represents a voltage demodulated by the demodulator 140. The demodulator 140 demodulates the signal 235, using the third frequency $f_3$. The third frequency $f_3$ is the frequency $f_1-f_2$, which is the difference between the first frequency $f_1$ and the second frequency $f_2$.

A signal 237 is a demodulated form of the signal 235. By the operation of the demodulator 140 using the third frequency $f_3$, a signal 239 is also generated. Also, other signals 234 and 236 than the signal 235 are modulated by the operation of the demodulator 140 using the third frequency $f_3$. For example, a signal 238 is a modulated form of the signal 234, and a signal 240 is a modulated form of the signal 236.

A graph (v) of FIG. 2D represents a voltage filtered by the filter 150. The filter 150 passes signals of only a predetermined frequency or lower. The predetermined frequency is adapted to pass only the signal 237 but interrupt other signals 238, 239, and 240. For example, the predetermined frequency may be the third frequency $f_3$, that is, $f_1-f_2$. A signal 241 is substantially the same signal as the signal 237, that is, an output signal of the bio impedance measurement apparatus 100.

Thus, the bio impedance measurement apparatus 100 may provide a technology of measuring bio impedance while amplifying a band of the frequency $f_1-f_2$ lower than the first frequency $f_1$ corresponding to the bio impedance to be measured. Accordingly, the bio impedance measurement apparatus 100 may provide a technology of reducing power consumption needed for measurement of the bio impedance.

Figure 3A:
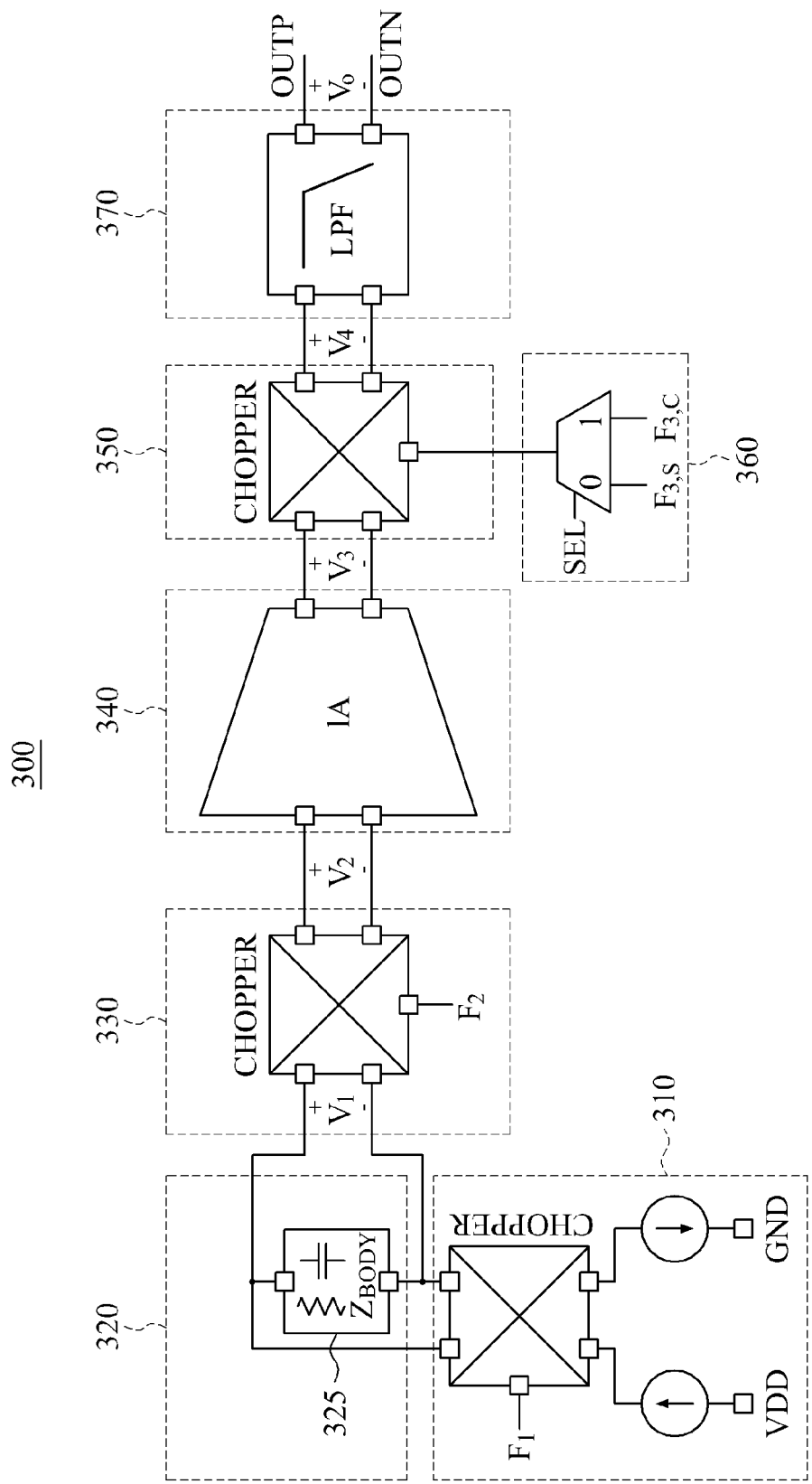
FIGS. 3A and 3B are circuit diagrams illustrating examples of a bio impedance measurement circuit.
Figure 3B:
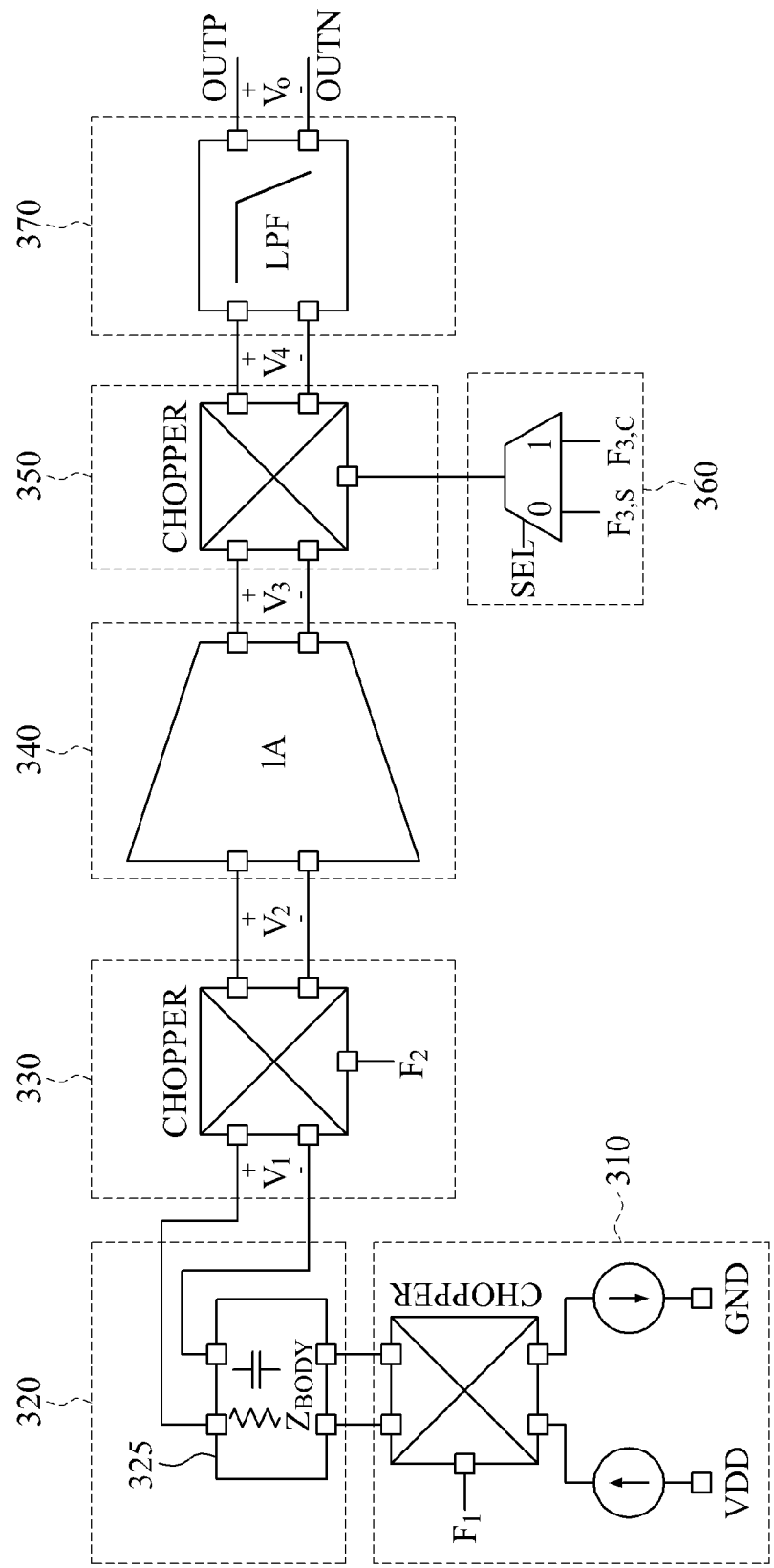

FIGS. 3A and 3B are circuit diagrams illustrating examples of a bio impedance measurement circuit 300. Referring to FIG. 3A, the bio impedance measurement circuit 300 includes a current applicator 310, a contactor 320, an intermediate modulator 330, an amplifier 340, a demodulator 350, a selector 360, and a filter 370.

A modulator included in the current applicator 310 includes a chopper. The chopper modulates a sourcing current source and a sinking current source. A frequency of the chopper that modulates the current sources may be determined according to a first frequency $f_1$.

A first frequency signal $F_1$ of the chopper that corresponds to the first frequency $f_1$ may be implemented by a square wave or a sine wave. When only a fundamental term excluding harmonics is considered among frequency components of the first frequency signal $F_1$, the first frequency signal $F_1$ may be expressed by Equation 1. For a concise expression, an amplitude of the first frequency signal $F_1$ may be presumed to be 1.

$$F_1 = \sin(2\pi \cdot f_1 t) \quad \text{[Equation 1]}$$

In Equation 1, $F_1$ denotes the first frequency signal, $f_1$ denotes the first frequency, and t denotes a time.

When a current output from the current applicator 310 is injected to a living body 325 through the contactor 320, a first voltage $V_1$ according to a bio impedance is generated. As aforementioned with reference to FIGS. 1C and 1D, a plurality of terminals included in the contactor 320 of FIG. 3A are connected to the living body 325 according to the 2-terminal measurement method, and a plurality of terminals included in the contactor 320 of FIG. 3B are connected to the living body 325 according to the 4-terminal measurement method.

The intermediate modulator 330 includes a chopper. The chopper outputs a second voltage $V_2$ by modulating the first voltage $V_1$. A frequency of the chopper that modulates the first voltage $V_1$ may be determined by a second frequency $f_2$.

A second frequency signal $F_2$ of the chopper that corresponds to the second frequency $f_2$ may be implemented by a square wave or a sine wave. Considering only a fundamental term excluding harmonics among frequency components of the second frequency signal $F_2$, the second frequency signal $F_2$ may be expressed by Equation 2. For a concise expression, an amplitude of the second frequency signal $F_2$ may be presumed to be 1.

$$F_2 = \sin(2\pi \cdot f_2 t) \quad \text{[Equation 2]}$$

In Equation 2, $F_2$ denotes the second frequency signal, $f_2$ denotes the second frequency, and t denotes the time.

The amplifier 340 includes an IA. The IA outputs a third voltage $V_3$ by amplifying the second voltage $V_2$.

The demodulator 350 includes a chopper. The chopper outputs a fourth voltage $V_4$ by demodulating the third voltage $V_3$. A frequency of the chopper that demodulates the third voltage $V_3$ may be determined by a third frequency $f_3$.

The selector 360 includes a multiplexer (MUX). The MUX selects any one of a plurality of signals depending on a select signal SEL. For example, the MUX may select any one of two signals having a phase difference of about 90 degrees, depending on the select signal SEL. However, the phase difference is not limited to 90 degrees. For example, the phase difference may range from 0 degrees to 180 degrees, depending on purposes. Hereinafter, an example in which two signals having a phase difference of about 90 degrees are used will be described.

The MUX selects any one of a third sine signal $F_{3,S}$ and a third cosine signal $F_{3,C}$ depending on the select signal SEL. In this example, the MUX selects the third sine signal $F_{3,S}$ when the select signal SEL is a logical value 0, and selects the third cosine signal $F_{3,C}$ when the select signal SEL is a logical value 1.

The third sine signal $F_{3,S}$ and the third cosine signal $F_{3,C}$ may both correspond to the third frequency $f_3$. However, the phase difference between the third sine signal $F_{3,S}$ and the third cosine signal $F_{3,C}$ may be approximately 90 degrees. That is, although each of a frequency of the third sine signal $F_{3,S}$ and a frequency of the third cosine signal $F_{3,C}$ is the third frequency $f_3$, the phase difference between the third sine signal $F_{3,S}$ and the third cosine signal $F_{3,C}$ may be approximately 90 degrees.

Each of the third sine signal $F_{3,S}$ and a frequency of the third cosine signal $F_{3,C}$ may be implemented by a square wave or a sine wave. Considering only a fundamental term excluding harmonics among frequency components of the third sine signal $F_{3,S}$, the third sine signal $F_{3,S}$ may be expressed by Equation 3. For a concise expression, an amplitude of the third sine signal $F_{3,S}$ may be presumed to be 1.

$$F_{3,S} = \sin(2\pi \cdot f_3 t) \quad \text{[Equation 3]}$$

In Equation 3, $F_{3,S}$ denotes the third sine signal, $f_3$ denotes the third frequency, and t denotes the time. The third frequency $f_3$ may be the frequency $f_1 - f_2$ that is a difference between the first frequency $f_1$ and the second frequency $f_2$.

Considering only a fundamental term excluding harmonics among frequency components of the third cosine signal $F_{3,C}$, the third cosine signal $F_{3,C}$ may be expressed by Equation 4. For a concise expression, an amplitude of the third cosine signal $F_{3,C}$ may be presumed to be 1.

$$F_{3,C} = \cos(2\pi \cdot f_3 t) \quad \text{[Equation 4]}$$

In Equation 4, $F_{3,C}$ denotes the third cosine signal, $f_3$ denotes the third frequency, and t denotes the time. The third frequency $f_3$ may be the frequency $f_1 - f_2$ that is the difference between the first frequency $f_1$ and the second frequency $f_2$.

The filter 370 includes an LPF. The LPF cancels high frequency components included in the fourth voltage $V_4$, and finally outputs an output voltage $V_O$ via terminals OUTP and OUTN.

Hereinafter, an operation principle of the bio impedance measurement circuit 300 will be described in detail. For example, the bio impedance measurement circuit 300 may measure a real component $Z_{RE}$ of the bio impedance.

The chopper of the current applicator 310 is driven by the first frequency signal $F_1$. The first voltage $V_1$ may be generated by the current output by the current applicator 310 and the real component $Z_{RE}$ of the bio impedance. The first voltage $V_1$ may be expressed by Equation 5.

$$V_1 = Z_{RE} \cdot I \cdot \sin(2\pi \cdot f_1 t) \quad \text{[Equation 5]}$$

In Equation 5, $V_1$ denotes the first voltage, $Z_{RE}$ denotes the real component of the bio impedance, I denotes a magnitude of a current supplied by a current source, $f_1$ denotes the first frequency, and t denotes the time. The first frequency $f_1$ may be a fundamental frequency of the first frequency signal $F_1$.

The chopper of the intermediate modulator 330 is driven by the second frequency signal $F_2$. The first voltage $V_1$ is modulated into the second voltage $V_2$ through the chopper of the intermediate modulator 330. The second voltage $V_2$ may be expressed by Equation 6.

$$V_2 = V_1 \cdot F_2 \quad \text{[Equation 6]}$$

$$= -\frac{1}{2} Z_{RE} \cdot I \cdot \{\cos(2\pi \cdot (f_1 + f_2)t) - \cos(2\pi \cdot (f_1 - f_2)t)\}$$

In Equation 6, $V_1$ denotes the first voltage, $V_2$ denotes the second voltage, $F_2$ denotes the second frequency signal, $Z_{RE}$ denotes the real component of the bio impedance, I denotes the magnitude of the current supplied by the current source, $f_1$ denotes the first frequency, t denotes the time, and $f_2$ denotes the second frequency. The first frequency $f_1$ may be the fundamental frequency of the first frequency signal $F_1$. The second frequency $f_2$ may be the fundamental frequency of the second frequency signal $F_2$.

The IA of the amplifier 340 amplifies the second voltage $V_2$, and outputs the third voltage $V_3$. The third voltage $V_3$ may be expressed by Equation 7.

$$V_3 = A \cdot V_2 \quad \text{[Equation 7]}$$

$$= -\frac{1}{2} A \cdot Z_{RE} \cdot I \cdot \{\cos(2\pi \cdot (f_1 + f_2)t) - \cos(2\pi \cdot (f_1 - f_2)t)\}$$

In Equation 7, $V_2$ denotes the second voltage, $V_3$ denotes the third voltage, A denotes a voltage gain of the IA, $Z_{RE}$ denotes the real component of the bio impedance, I denotes the magnitude of the current supplied by the current source, $f_1$ denotes the first frequency, $f_2$ denotes the second frequency, and t denotes the time. The first frequency $f_1$ may be the fundamental frequency of the first frequency signal $F_1$. The second frequency $f_2$ may be the fundamental frequency of the second frequency signal $F_2$.

The chopper of the demodulator 350 is driven by the third cosine signal $F_{3,C}$ or the third sine signal $F_{3,S}$. The chopper of the demodulator 350 outputs the fourth voltage $V_4$ by demodulating the third voltage $V_3$. The MUX of the selector 360 selects the third cosine signal $F_{3,C}$ or the third sine signal $F_{3,S}$ to be provided to the chopper of the demodulator 350. To detect the real component $Z_{RE}$ of the bio impedance, the MUX of the selector 360 selects the third cosine signal $F_{3,C}$ between the third sine signal $F_{3,S}$ and the third cosine signal $F_{3,C}$. In this example, the fourth voltage $V_4$ may be expressed by Equation 8.

$$V_4 = V_3 \cdot F_{3,C} \quad \text{[Equation 8]}$$

$$= -\frac{1}{4} A \cdot Z_{RE} \cdot I \cdot \{\cos(2\pi \cdot 2f_1 t) + \cos(2\pi \cdot 2f_2 t) -$$

$$\cos(2\pi \cdot 2(f_1 - f_2)t) - \cos(0)\}$$

In Equation 7, $V_3$ denotes the third voltage, $V_4$ denotes the fourth voltage, $F_{3,C}$ denotes the third cosine signal, A denotes the voltage gain of the IA, $Z_{RE}$ denotes the real component of the bio impedance, I denotes the magnitude of the current supplied by the current source, $f_1$ denotes the first frequency, $f_2$ denotes the second frequency, and t denotes the time. The third frequency $f_3$ may be a fundamental frequency of the third cosine signal $F_{3,C}$, that is, the frequency $f_1-f_2$ that is the difference between the first frequency $f_1$ and the second frequency $f_2$. The first frequency $f_1$ may be the fundamental frequency of the first frequency signal $F_1$. The second frequency $f_2$ may be the fundamental frequency of the second frequency signal $F_2$.

The LPF of the filter 370 passes signals of only a band of a cutoff frequency or lower. When the cutoff frequency is the third frequency $f_3$, the output voltage $V_0$ of the filter 370 may be expressed by Equation 9.

$$V_o = \frac{1}{4} A \cdot Z_{RE} \cdot I \qquad \text{[Equation 9]}$$

In Equation 9, $V_O$ denotes the output voltage, A denotes the voltage gain of the IA, $Z_{RE}$ denotes the real component of the bio impedance, and I denotes the magnitude of the current supplied by the current source. Referring to Equation 9, the output voltage $V_O$ may be determined by the input current I, the voltage gain A of the IA, and the real component $Z_{RE}$ of the bio impedance.

As aforementioned, the IA of the amplifier 340 amplifies only frequency components included in a bandwidth of the IA, instead of amplifying all frequency components of the second voltage $V_2$. For example, the bandwidth of the amplifier 340 may not include a band corresponding to the frequency $f_1+f_2$, but include a band corresponding to the frequency $f_1-f_2$. In this example, Equation 7 may be approximated to Equation 10.

$$V_3 = A \cdot V_2 \approx -\frac{1}{2} A \cdot Z_{RE} \cdot I \cdot \{-\cos(2\pi \cdot (f_1 - f_2)t)\} \qquad \text{[Equation 10]}$$

In Equation 10, $V_2$ denotes the second voltage, $V_3$ denotes the third voltage, A denotes the voltage gain of the IA, $Z_{RE}$ denotes the real component of the bio impedance, I denotes the magnitude of the current supplied by the current source, $f_1$ denotes the first frequency, $f_2$ denotes the second frequency, and t denotes the time. The first frequency $f_1$ may be the fundamental frequency of the first frequency signal $F_1$. The second frequency $f_2$ may be the fundamental frequency of the second frequency signal $F_2$.

In this example, Equation 8 may be approximated to Equation 11.

$$V_4 = \qquad \text{[Equation 11]}$$
$$V_3 \cdot F_{3,C} \approx -\frac{1}{4} A \cdot Z_{RE} \cdot I \cdot \{-\cos(2\pi \cdot 2(f_1 - f_2)t) - \cos(0)\}$$

In Equation 11, $V_3$ denotes the third voltage, $V_4$ denotes the fourth voltage, $F_{3,C}$ denotes the third cosine signal, A denotes the voltage gain of the IA, $Z_{RE}$ denotes the real component of the bio impedance, I denotes the magnitude of the current supplied by the current source, $f_1$ denotes the first frequency, $f_2$ denotes the second frequency, and t denotes the time. The third frequency $f_3$ may be a fundamental frequency of the third cosine signal $F_{3,C}$, that is, the frequency $f_1-f_2$ that is the difference between the first frequency $f_1$ and the second frequency $f_2$. The first frequency $f_1$ may be the fundamental frequency of the first frequency signal $F_1$. The second frequency $f_2$ may be the fundamental frequency of the second frequency signal $F_2$.

Even when Equation 7 and Equation 8 are approximated to Equation 10 and Equation 11, respectively, the output voltage $V_O$ may be expressed in the same way as in Equation 9. Thus, although the bandwidth of the IA of the amplifier 340 is reduced, the bio impedance may be accurately measured.

As another example, the bio impedance measurement circuit 300 may measure an imaginary component $Z_{IM}$ of the bio impedance.

The chopper of the current applicator 310 is driven by the first frequency signal $F_1$. The first voltage $V_1$ may be generated by the current output by the current applicator 310 and the imaginary component $Z_{IM}$ of the bio impedance. The first voltage $V_1$ may be expressed by Equation 12.

$$V_1 = Z_{IM} \cdot I \cdot \cos(2\pi \cdot f_1 t) \qquad \text{[Equation 12]}$$

In Equation 12, $V_1$ denotes the first voltage, $Z_{IM}$ denotes the imaginary component of the bio impedance, I denotes the magnitude of the current supplied by the current source, $f_1$ denotes the first frequency, and t denotes the time. The first frequency $f_1$ may be the fundamental frequency of the first frequency signal $F_1$.

The chopper of the intermediate modulator 330 is driven by the second frequency signal $F_2$. The first voltage $V_1$ is modulated into the second voltage $V_2$ through the chopper of the intermediate modulator 330. The second voltage $V_2$ may be expressed by Equation 13.

$$V_2 = V_1 \cdot F_2 \qquad \text{[Equation 13]}$$
$$= \frac{1}{2} Z_{IM} \cdot I \cdot \left\{ \begin{array}{l} \sin(2\pi \cdot (f_1 + f_2)t) - \\ \sin(2\pi \cdot (f_1 - f_2)t) \end{array} \right\}$$

In Equation 12, $V_1$ denotes the first voltage, $V_2$ denotes the second voltage, $F_2$ denotes the second frequency signal, $Z_{IM}$ denotes the imaginary component of the bio impedance, I denotes the magnitude of the current supplied by the current source, $f_1$ denotes the first frequency, t denotes the time, and $f_2$ denotes the second frequency. The first frequency $f_1$ may be the fundamental frequency of the first frequency signal $F_1$. The second frequency $f_2$ may be the fundamental frequency of the second frequency signal $F_2$.

The IA of the amplifier 340 outputs the third voltage $V_3$ by amplifying the second voltage $V_2$. The third voltage $V_3$ may be expressed by Equation 14.

$$V_3 = A \cdot V_2 \qquad \text{[Equation 14]}$$
$$= \frac{1}{2} A \cdot Z_{IM} \cdot I \cdot \left\{ \begin{array}{l} \sin(2\pi \cdot (f_1 + f_2)t) - \\ \sin(2\pi \cdot (f_1 - f_2)t) \end{array} \right\}$$

In Equation 14, $V_2$ denotes the second voltage, $V_3$ denotes the third voltage, A denotes the voltage gain of the IA, $Z_{IM}$ denotes the imaginary component of the bio impedance, I denotes the magnitude of the current supplied by the current source, $f_1$ denotes the first frequency, $f_2$ denotes the second frequency, and t denotes the time. The first frequency $f_1$ may be the fundamental frequency of the first frequency signal $F_1$. The second frequency $f_2$ may be the fundamental frequency of the second frequency signal $F_2$.

The chopper of the demodulator 350 is driven by the third cosine signal $F_{3,C}$ or the third sine signal $F_{3,S}$. The chopper of the demodulator 350 outputs the fourth voltage $V_4$ by demodulating the third voltage $V_3$. The MUX of the selector 360 selects the third cosine signal $F_{3,C}$ or the third sine signal $F_{3,S}$ to be provided to the chopper. To detect the imaginary component $Z_{IM}$ of the bio impedance, the MUX of the selector 360 selects the third sine signal $F_{3,S}$ between the third sine signal $F_{3,S}$ and the third cosine signal $F_{3,C}$. In this example, the fourth voltage $V_4$ may be expressed by Equation 15.

$$V_4 = V_3 \cdot F_{3,S} \quad\quad\quad \text{[Equation 15]}$$
$$= -\frac{1}{4} A \cdot Z_{IM} \cdot I \cdot \left\{ \begin{array}{c} \cos(2\pi \cdot 2f_1 t) - \\ \cos(2\pi \cdot 2f_2 t) - \\ \cos(2\pi \cdot 2(f_1 - f_2)t) + \cos(0) \end{array} \right\}$$

In Equation 15, $V_3$ denotes the third voltage, $V_4$ denotes the fourth voltage, $F_{3,S}$ denotes the third sine signal, A denotes the voltage gain of the IA, $Z_{IM}$ denotes the imaginary component of the bio impedance, I denotes the magnitude of the current supplied by the current source, $f_1$ denotes the first frequency, $f_2$ denotes the second frequency, and t denotes the time. The third frequency $f_3$ may be the fundamental frequency of the third sine signal $F_{3,S}$, that is, the frequency $f_1-f_2$ that is the difference between the first frequency $f_1$ and the second frequency $f_2$. The first frequency $f_1$ may be the fundamental frequency of the first frequency signal $F_1$. The second frequency $f_2$ may be the fundamental frequency of the second frequency signal $F_2$.

The LPF of the filter 370 passes only signals of a band of a cutoff frequency or lower. When the cutoff frequency is the third frequency $f_3$, the output voltage $V_0$ of the filter 370 may be expressed by Equation 16.

$$V_o = \frac{1}{4} A \cdot Z_{IM} \cdot I \quad\quad\quad \text{[Equation 16]}$$

In Equation 16, $V_0$ denotes the output voltage, A denotes the voltage gain of the IA, $Z_{IM}$ denotes the imaginary component of the bio impedance, and I denotes the magnitude of the current supplied by the current source. Referring to Equation 16, the output voltage $V_0$ may be determined by the input current I, the voltage gain A of the IA, and the imaginary component $Z_{IM}$ of the bio impedance.

As aforementioned, the IA of the amplifier 340 amplifies only frequency components included in the bandwidth of the IA, instead of amplifying all frequency components of the second voltage V2. For example, the bandwidth of the IA may not include a band corresponding to the frequency $f_1+f_2$, but include a band corresponding to the frequency $f_1-f_2$. Therefore, Equation 14 may be approximated to Equation 17.

$$V_3 = A \cdot V_2 \approx \frac{1}{2} A \cdot Z_{IM} \cdot I \cdot \{-\sin(2\pi \cdot (f_1 - f_2)t)\} \quad \text{[Equation 17]}$$

In Equation 17, $V_2$ denotes the second voltage, $V_3$ denotes the third voltage, A denotes the voltage gain of the IA, $Z_{IM}$ denotes the imaginary component of the bio impedance, I denotes the magnitude of the current supplied by the current source, $f_1$ denotes the first frequency, $f_2$ denotes the second frequency, and t denotes the time. The first frequency $f_1$ may be the fundamental frequency of the first frequency signal $F_1$. The second frequency $f_2$ may be the fundamental frequency of the second frequency signal $F_2$.

In this example, Equation 15 may be approximated to Equation 18.

$$V_4 = \quad\quad\quad \text{[Equation 18]}$$
$$V_3 \cdot F_{3,S} \approx -\frac{1}{4} A \cdot Z_{IM} \cdot I \cdot \{-\cos(2\pi \cdot 2(f_1 - f_2)t) + \cos(0)\}$$

In Equation 18, $V_3$ denotes the third voltage, $V_4$ denotes the fourth voltage, $F_{3,S}$ denotes the third sine signal, A denotes the voltage gain of the IA, $Z_{IM}$ denotes the imaginary component of the bio impedance, I denotes the magnitude of the current supplied by the current source, $f_1$ denotes the first frequency, $f_2$ denotes the second frequency, and t denotes the time. The third frequency $f_3$ may be the fundamental frequency of the third sine signal $F_{3,S}$, that is, the frequency $f_1-f_2$ that is the difference between the first frequency $f_1$ and the second frequency $f_2$. The first frequency $f_1$ may be the fundamental frequency of the first frequency signal $F_1$. The second frequency $f_2$ may be the fundamental frequency of the second frequency signal $F_2$.

Even when Equation 14 and Equation 15 are approximated to Equation 17 and Equation 18, respectively, the output voltage $V_0$ may be expressed in the same way as in Equation 16. Thus, although the bandwidth of the IA of the amplifier 340 is reduced, the bio impedance may be accurately measured.

In an example, when the first frequency $f_1$ corresponding to a type of the bio impedance to be measured is $2f_o$, the second frequency $f_2$ may be determined to be $f_o$. The third frequency $f_3$ may also be determined to be $f_o$. As aforementioned, the bio impedance measurement apparatus may accurately measure the bio impedance to be measured even when a frequency $f_c$ corresponding to the bandwidth of the IA is higher than $f_o$ but lower than $2f_o$. For example, when the first frequency $f_1$ is $2f_o$, and the second frequency $f_2$ and the third frequency $f_3$ are $2f_o$, requirements of the bandwidth of the IA may be reduced by half in comparison to a conventional impedance measurement method.

That is, when the first frequency is $2f_o$, and the second frequency and the third frequency are $2f_o$, the first frequency signal $F_1$, the second frequency signal $F_2$, the third sine signal $F_{3,S}$, and the third cosine signal $F_{3,C}$ may be expressed by Equation 19 to Equation 22, respectively.

$$F_1 = \sin(2\pi \cdot 2f_o t) \quad\quad\quad \text{[Equation 19]}$$

$$F_2 = \sin(2\pi f_o t) \quad\quad\quad \text{[Equation 20]}$$

$$F_{3,S} = \sin(2\pi f_o t) \quad\quad\quad \text{[Equation 21]}$$

$$F_{3,C} = \cos(2\pi f_o t) \quad\quad\quad \text{[Equation 22]}$$

In Equation 19 to Equation 22, $F_1$ denotes the first frequency signal, $F_2$ denotes the second frequency signal, $F_{3,S}$ denotes the third sine signal, $F_{3,C}$ denotes the third cosine signal, and t denotes the time.

When the real component $Z_{RE}$ of the bio impedance is measured, the first voltage $V_1$, the second voltage $V_2$, the third voltage $V_3$, and the fourth voltage $V_4$ may be expressed by Equation 23 to Equation 26, respectively.

$$V_1 = Z_{RE} \cdot I \cdot \sin(2\pi \cdot 2f_o t) \qquad \text{[Equation 23]}$$

$$V_2 = V_1 \cdot F_2 \qquad \text{[Equation 24]}$$
$$= -\frac{1}{2} Z_{RE} \cdot I \cdot \{\cos(2\pi \cdot 3f_o t) - \cos(2\pi \cdot f_o t)\}$$

$$V_3 = A \cdot V_2 \qquad \text{[Equation 25]}$$
$$= -\frac{1}{2} A \cdot Z_{RE} \cdot I \cdot \{\cos(2\pi \cdot 3f_o t) - \cos(2\pi \cdot f_o t)\}$$

$$V_4 = V_3 \cdot F_{3,C} \qquad \text{[Equation 26]}$$
$$= -\frac{1}{4} A \cdot Z_{RE} \cdot I \cdot \begin{Bmatrix} \cos(2\pi \cdot 4f_o t) + \\ \cos(2\pi \cdot 2f_o t) - \\ \cos(2\pi \cdot 2f_o t) - \cos(0) \end{Bmatrix}$$

In Equation 23 to Equation 26, $V_1$ denotes the first voltage, $V_2$ denotes the second voltage, $V_3$ denotes the third voltage, and $V_4$ denotes the fourth voltage. $Z_{RE}$ denotes the real component of the bio impedance, I denotes the magnitude of the current supplied by the current source, and t denotes the time. $F_2$ denotes the second frequency signal, $F_{3,C}$ denotes the third cosine signal, and A denotes the voltage gain of the IA.

Since the frequency $f_c$ corresponding to the bandwidth of the IA is higher than $f_o$ but lower than $2f_o$, an amplification level obtained in a frequency band higher than $2f_o$ may not be sufficient. In this example, Equation 25 and Equation 26 may be approximated to Equation 27 and Equation 28, respectively.

$$V_3 \approx -\frac{1}{2} A \cdot Z_{RE} \cdot I \cdot \{-\cos(2\pi \cdot f_o t)\} \qquad \text{[Equation 27]}$$

$$V_4 \approx -\frac{1}{4} A \cdot Z_{RE} \cdot I \cdot \{-\cos(2\pi \cdot f_o t) - \cos(0)\} \qquad \text{[Equation 28]}$$

In Equation 27 and Equation 28, $V_3$ denotes the third voltage, $V_4$ denotes the fourth voltage, A denotes the voltage gain of the IA, $Z_{RE}$ denotes the real component of the bio impedance, I denotes the magnitude of the current supplied by the current source, and t denotes the time.

Since the bandwidth of the IA is lower than the frequency $2f_o$, even when the third voltage $V_3$ and the fourth voltage $V_4$ are approximated to Equation 27 and Equation 28, the output voltage $V_o$ may be expressed by Equation 29 in the same manner as when the bandwidth of the IA is greater than or equal to $2f_o$.

$$V_o = \frac{1}{4} A \cdot Z_{RE} \cdot I \qquad \text{[Equation 29]}$$

In Equation 29, $V_o$ denotes the output voltage, A denotes the voltage gain of the IA, $Z_{RE}$ denotes the real component of the bio impedance, and I denotes the magnitude of the current supplied by the current source.

Therefore, according to the examples, power consumption reduction of the bio impedance measurement circuit may be achieved by using the IA having a relatively low bandwidth when measuring impedance of a frequency. In addition, bio impedance of a high frequency may be measured even with the IA having the low bandwidth.

When the imaginary component $Z_{IM}$ of the bio impedance is measured, the first voltage $V_1$, the second voltage $V_2$, the third voltage $V_3$, and the fourth voltage $V_4$ may be expressed by Equation 30 to Equation 33, respectively.

$$V_1 = Z_M \cdot I \cdot \cos(2\pi \cdot 2f_o t) \qquad \text{[Equation 30]}$$

$$V_2 = V_1 \cdot F_2 \qquad \text{[Equation 31]}$$
$$= \frac{1}{2} Z_{IM} \cdot I \cdot \{\sin(2\pi \cdot 3f_o t) - \sin(2\pi \cdot f_o t)\}$$

$$V_3 = A \cdot V_2 \qquad \text{[Equation 32]}$$
$$= \frac{1}{2} A \cdot Z_{IM} \cdot I \cdot \{\sin(2\pi \cdot 3f_o t) - \sin(2\pi \cdot f_o t)\}$$

$$V_4 = V_3 \cdot F_{3,S} \qquad \text{[Equation 33]}$$
$$= -\frac{1}{4} A \cdot Z_{IM} \cdot I \cdot \begin{Bmatrix} \cos(2\pi \cdot 4f_o t) - \\ \cos(2\pi \cdot 2f_o t) - \\ \cos(2\pi \cdot 2f_o t) + \cos(0) \end{Bmatrix}$$

In Equation 30 to Equation 33, $V_1$ denotes the first voltage, $V_2$ denotes the second voltage, $V_3$ denotes the third voltage, and $V_4$ denotes the fourth voltage. $Z_{IM}$ denotes the imaginary component of the bio impedance, I denotes the magnitude of the current supplied by the current source, and t denotes the time. $F_2$ denotes the second frequency signal, $F_{3,S}$ denotes the third sine signal, and A denotes the voltage gain of the IA.

Since the frequency $f_c$ corresponding to the bandwidth of the IA is higher than the frequency $f_o$ but lower than $2f_o$, an amplification level obtained in a frequency band higher than $2f_o$ may not be sufficient. In this example, Equation 32 and Equation 33 may be approximated to Equation 34 and Equation 35, respectively.

$$V_3 \approx \frac{1}{2} A \cdot Z_{IM} \cdot I \cdot \{-\sin(2\pi \cdot f_o t)\} \qquad \text{[Equation 34]}$$

$$V_4 \approx -\frac{1}{4} A \cdot Z_{IM} \cdot I \cdot \{-\cos(2\pi \cdot 2f_o t) + \cos(0)\} \qquad \text{[Equation 35]}$$

In Equation 34 and Equation 35, $V_3$ denotes the third voltage, $V_4$ denotes the fourth voltage, A denotes the voltage gain of the IA, $Z_{IM}$ denotes the imaginary component of the bio impedance, I denotes the magnitude of the current supplied by the current source, and t denotes the time.

Since the bandwidth of the IA is lower than the frequency $2f_o$, even when the third voltage $V_3$ and the fourth voltage $V_4$ are approximated to Equation 34 and Equation 35, the output voltage $V_o$ may be expressed by Equation 36 in the same manner as when the bandwidth of the IA is greater than or equal to $2f_o$.

$$V_o = \frac{1}{4} A \cdot Z_{IM} \cdot I \qquad \text{[Equation 36]}$$

In Equation 36, $V_o$ denotes the output voltage, A denotes the voltage gain of the IA, $Z_{IM}$ denotes the imaginary component of the bio impedance, and I denotes the magnitude of the current supplied by the current source.

Therefore, according to the examples, power consumption reduction of the bio impedance measurement circuit may be achieved by using the IA having a relatively low bandwidth when measuring impedance of a frequency. In addition, bio impedance of a high frequency may be measured even with the IA having the low bandwidth.

In the above description, the choppers illustrated in FIGS. 3A and 3B may be implemented by a multiplier.

FIG. 4 is a block diagram illustrating an example of a bio impedance measurement apparatus 400 further including a controller 160. Referring to FIG. 4, the bio impedance measurement apparatus 400 includes the current applicator 110, the contractor 115, the intermediate modulator 120, the amplifier 130, the demodulator 140, the selector 145, and the filter 150, of FIG. 1, further includes the controller 160.

The controller 160 determines a first frequency used in the current applicator 110, a second frequency used in the intermediate modulator 120, and a third frequency used in the demodulator 140.

For example, the controller 160 may determine the first frequency based on a type of a bio impedance to be measured. The controller 160 may use a mapping table in determining the first frequency. When the type of the bio impedance to be measured is determined, the controller 160 may determine a frequency corresponding to the type of the bio impedance, using the mapping table. The controller 160 may determine the frequency corresponding to the type of the bio impedance to be the first frequency.

The controller 160 may determine the third frequency based on a specification of the amplifier 130. For example, the controller 160 may determine the third frequency so that a signal of the third frequency to be demodulated by the demodulator 140 is fully amplified by the amplifier 130. In this example, the controller 160 may determine the second frequency based on the first frequency and the third frequency. For example, the controller 160 may determine the second frequency to be a frequency that is a difference between the first frequency and the third frequency.

Alternatively, the controller 160 may determine the second frequency so that an output signal of the intermediate modulator 120 is included in a bandwidth of the IA of the amplifier 130. That is, the controller 160 may determine the second frequency so that a frequency having a value obtained by subtracting the second frequency from the first frequency is lower than or equal to a frequency $f_c$ corresponding to the bandwidth of the amplifier. In this example, the controller 160 may determine the third frequency based on the first frequency and the second frequency. For example, the controller 160 may determine the third frequency to be the frequency that is a difference between the first frequency and the second frequency.

Although not shown in the drawings, the controller 160 may further include a frequency generator. The frequency generator may generate a first frequency signal corresponding to the first frequency, a second frequency signal corresponding to the second frequency, a third sine signal corresponding to the third frequency, and a third cosine signal corresponding to the third frequency. The controller 160 may provide the first frequency signal to the current applicator 110, the second frequency signal to the intermediate modulator 120, and the third sine signal and the third cosine signal to the selector 145.

The controller 160 may provide a select signal SEL for controlling the MUX of the selector 145. The controller 160 may provide a select signal SEL having a first logical value to the selector 145 to measure a real component of the bio impedance. In addition, the controller 160 may provide a select signal SEL having a second logical value to the selector 145 to measure an imaginary component of the bio impedance.

The controller 160 may alternately provide the select signal SEL having the first logical value and the select signal SEL having the second logical signal to the selector 145 at a predetermined period. In this example, the selector 145 may alternately select the third sine signal and the third cosine signal at the predetermined period. The demodulator 140 may alternately demodulate the real component and the imaginary component of the bio impedance at the predetermined period.

Figure 5A:
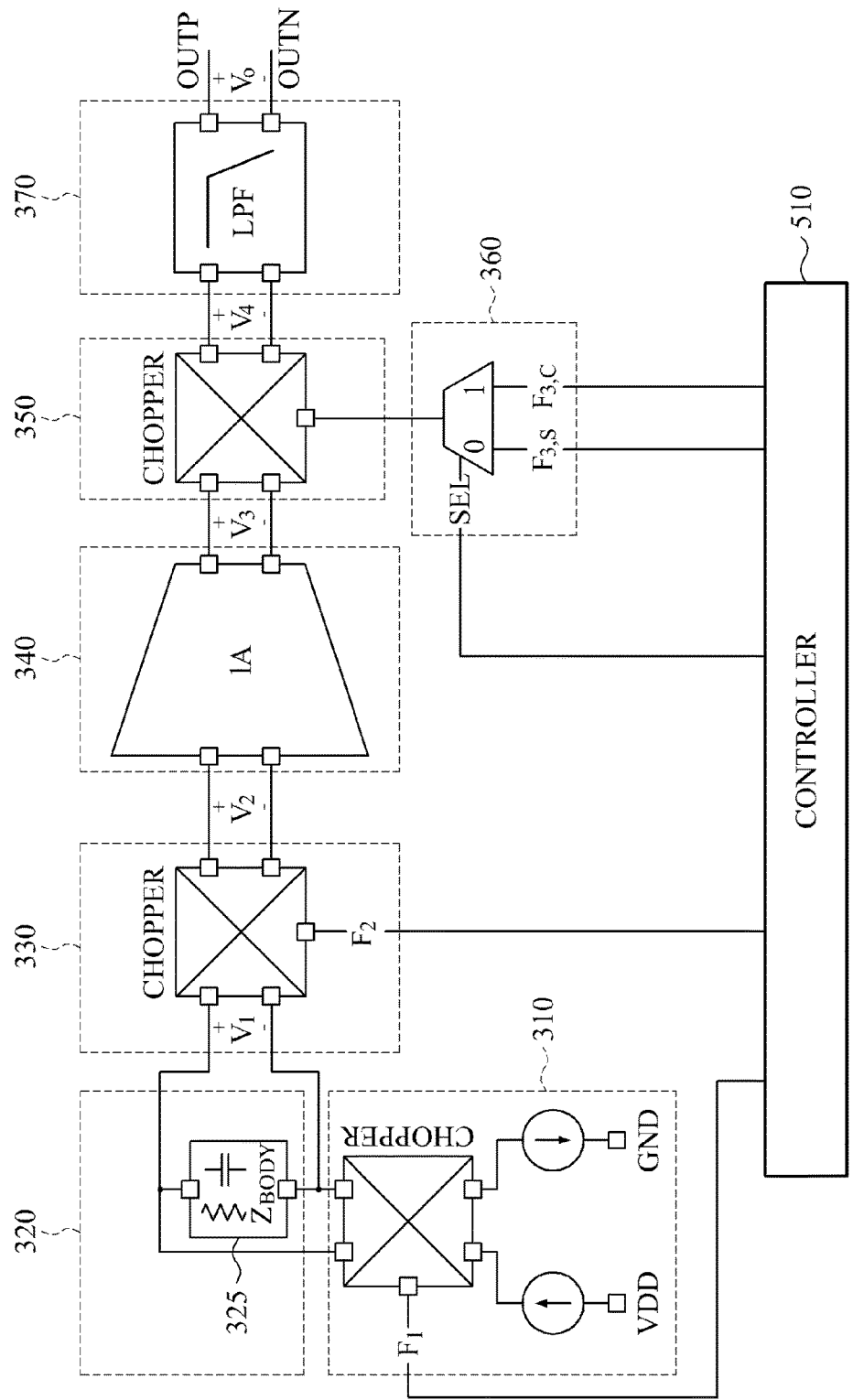
FIGS. 5A and 5B are circuit diagrams illustrating examples of a bio impedance measurement circuit further including a controller.
Figure 5B:
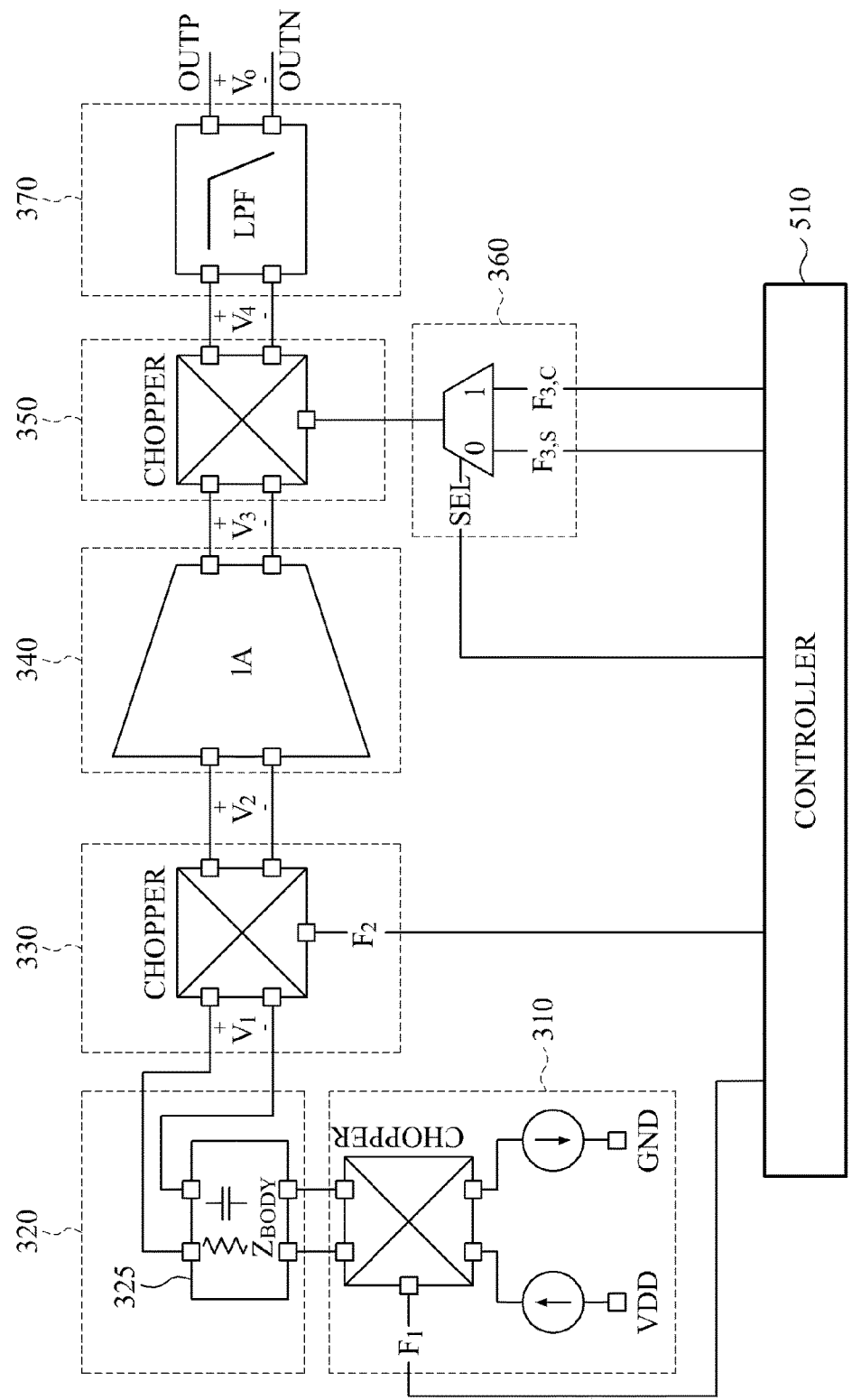

FIGS. 5A and 5B are circuit diagrams illustrating examples of a bio impedance measurement circuit 500 further including a controller 510. Referring to FIGS. 5A and 5B, the bio impedance measurement circuit 500 includes the current applicator 310, the contactor 320, the intermediate modulator 330, the amplifier 340, the demodulator 350, the selector 360, and the filter 370, of FIGS. 3A and 3B, further includes the controller 510.

The controller 510 provides the first frequency signal $F_1$ to the chopper included in the current applicator 310. The controller 510 provides the second frequency signal $F_2$ to the chopper included in the intermediate modulator 330. The controller 510 provides the third sine signal $F_{3,S}$ and the third cosine signal $F_{3,C}$ to the MUX included in the selector 360. The controller 510 provides the select signal SEL to the MUX of the selector 360. Since technical features illustrated with reference to FIGS. 3A, 3B, and 4 may be directly applied, a detailed description will be omitted.

Two terminals included in the contactor 320 of FIG. 5A are connected to the living body 325 according to the 2-terminal measurement method. Four terminals included in the contactor 320 of FIG. 5B are connected to the living body 325 according to the 4-terminal measurement method.

Figure 6:
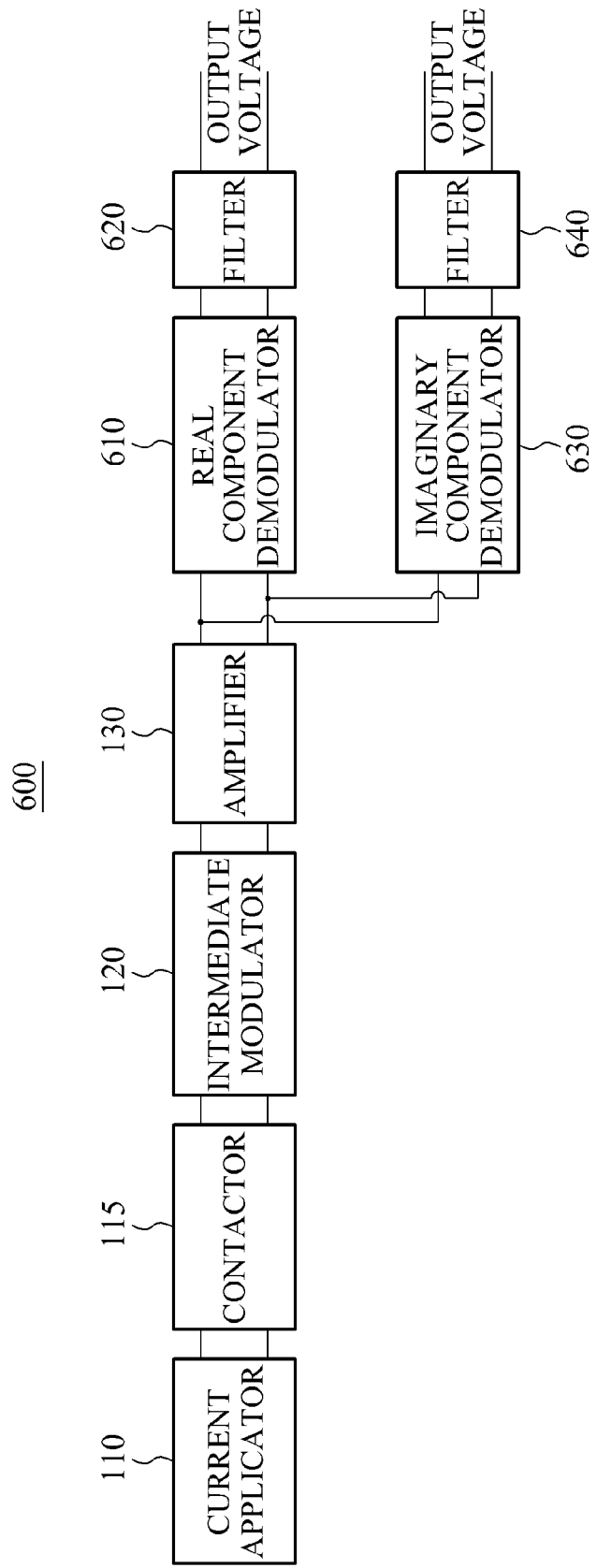
FIG. 6 is a block diagram illustrating an example of a bio impedance measurement apparatus including a plurality of demodulators.

FIG. 6 is a block diagram illustrating an example of a bio impedance measurement apparatus 600 including a plurality of demodulators. Referring to FIG. 6, the bio impedance measurement apparatus 600 includes the current applicator 110, the contactor 115, the intermediate modulator 120, and the amplifier 130, of FIG. 1, and includes a real component demodulator 610 and an imaginary component demodulator 630, separately.

The real component demodulator 610 demodulates an output signal of the amplifier 130 to measure a real component of a bio impedance. The imaginary component demodulator 630 demodulates the output signal of the amplifier 130 to measure an imaginary component of a bio impedance.

A filter 620 cancels high frequency components of an output signal of the real component demodulator 610 to generate a first output voltage. A filter 640 cancels high frequency components of an output signal of the imaginary component demodulator 630 to generate a second output voltage.

Since the real component demodulator 610 and the imaginary component demodulator 630 may apply the technical features illustrated with reference to FIGS. 1A to 3B, a detailed description will be omitted.

Figure 7A:
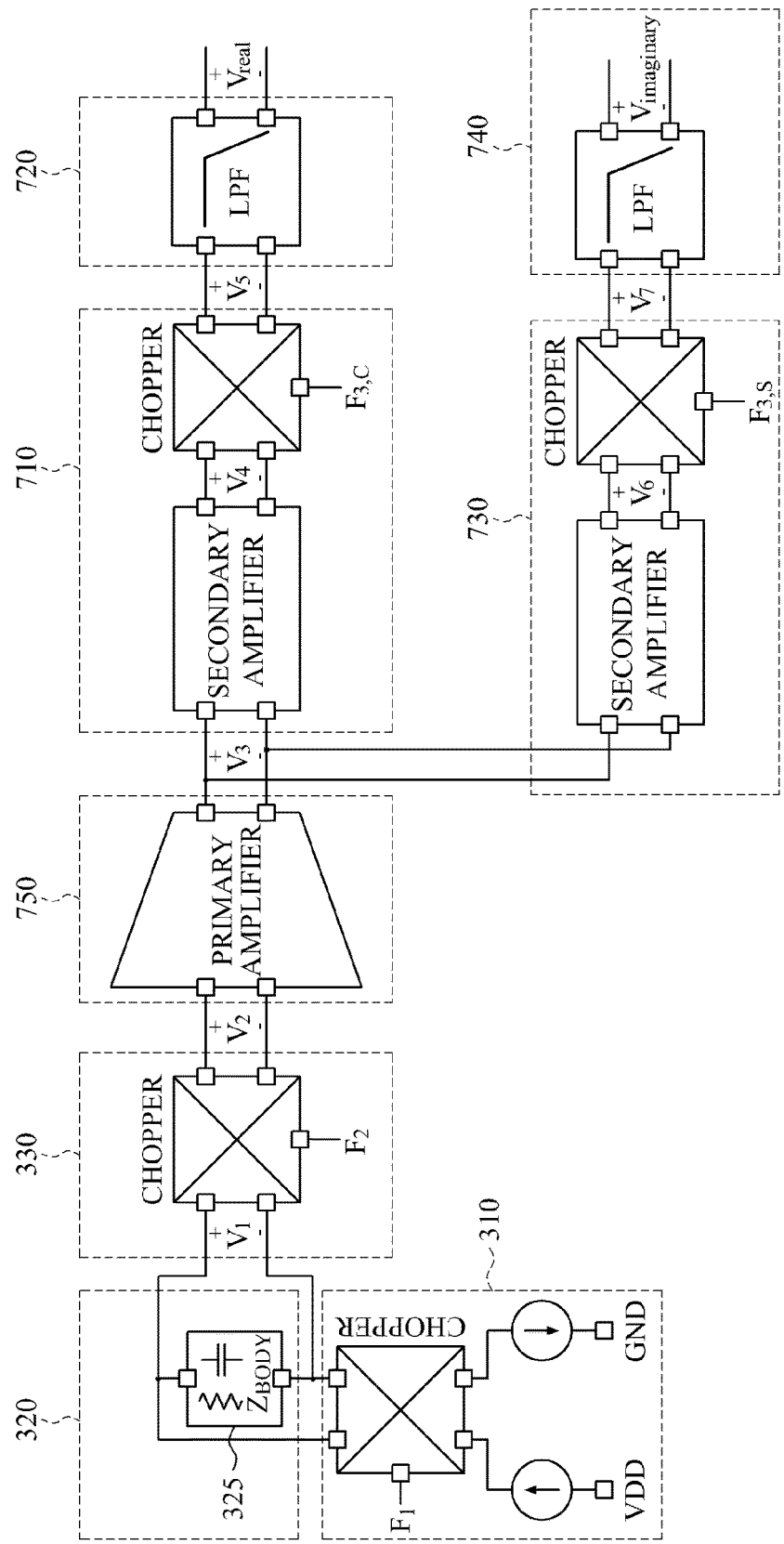
FIGS. 7A and 7B are circuit diagrams illustrating examples of a bio impedance measurement circuit including a plurality of demodulators.
Figure 7B:
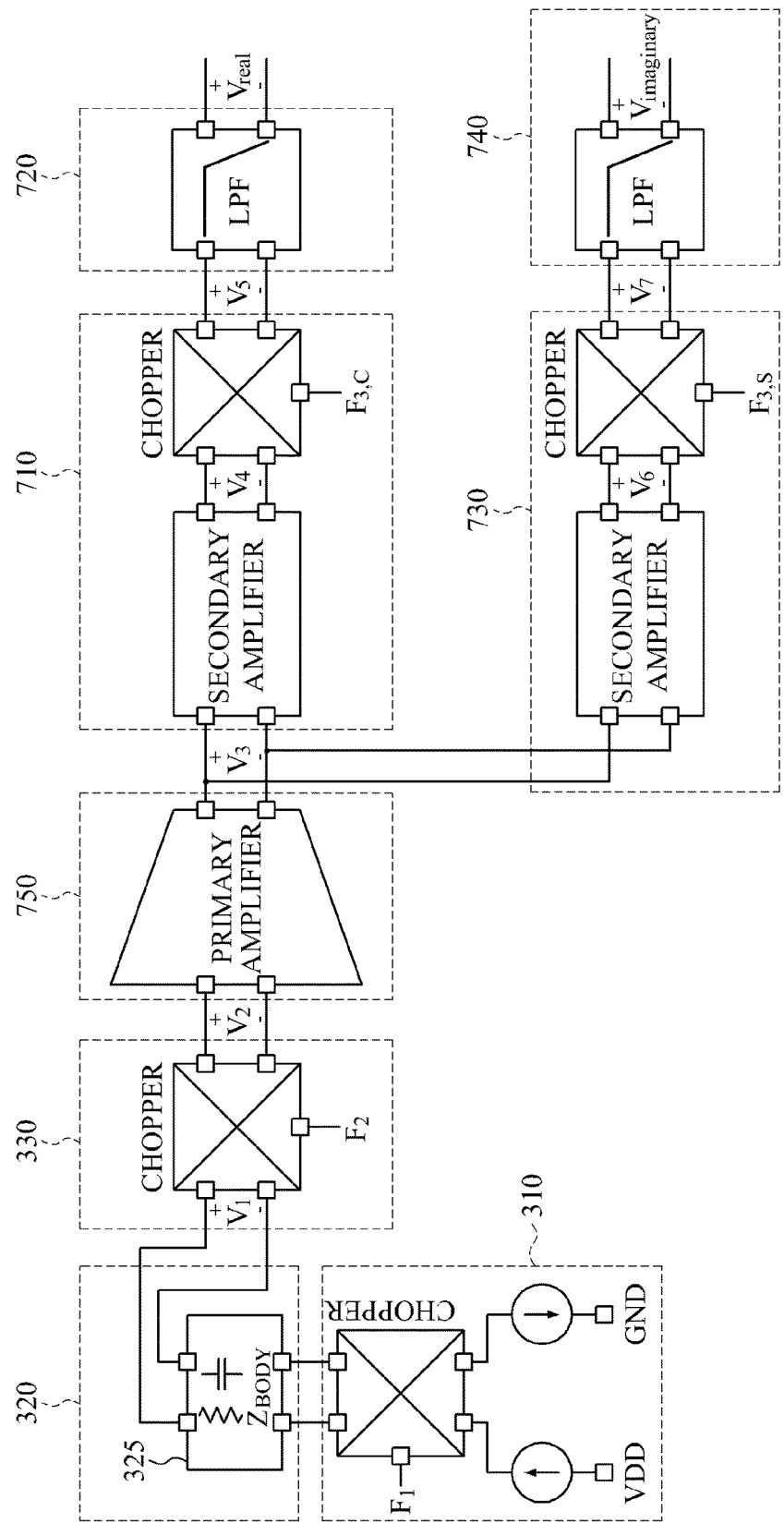

FIGS. 7A and 7B are circuit diagrams illustrating examples of a bio impedance measurement circuit 700 including a plurality of demodulators. Referring to FIGS. 7A and 7B, the bio impedance measurement circuit 700 includes the current applicator 310, the contactor 320, and the intermediate modulator 330, of FIGS. 3A and 3B, and further includes a primary amplifier 750, a first demodulator 710, a first filter 720, a second demodulator 730, and a second filter 740. The first demodulator 710 and the second demodulator 730 each include a secondary amplifier and a chopper. The first filter 720 and the second filter 740 each include an LPF. The chopper of the first demodulator 710 and the chopper of the second demodulator 730 are input with an output of an IA included in the primary amplifier 750.

The secondary amplifier of the first demodulator 710 outputs the fourth voltage $V_4$ by amplifying the third voltage $V_3$. The chopper of the first demodulator 710 generates a fifth voltage $V_5$ by demodulating the fourth voltage $V_4$, using the third cosine signal $F_{3,C}$, to measure the real component of the bio impedance. The secondary amplifier of the second demodulator 730 outputs a sixth voltage $V_6$ by amplifying the third voltage $V_3$, and the chopper of the second demodulator 730 generates a seventh voltage $V_7$ by demodulating the sixth voltage $V_6$, using the third sine signal $F_{3,S}$, to measure the imaginary component of the bio impedance. Since the technical features illustrated with reference to FIGS. 1A to 3B and 6 may be directly applied to the chopper of the first demodulator 710 and the chopper of the second demodulator 730, a detailed description will be omitted.

Two terminals of the contactor 320 of FIG. 7A are connected to the living body 325 according to the 2-terminal measurement method. Four terminals of the contactor 320 of FIG. 7B are connected to the living body 325 according to the 4-terminal measurement method.

Figure 8:
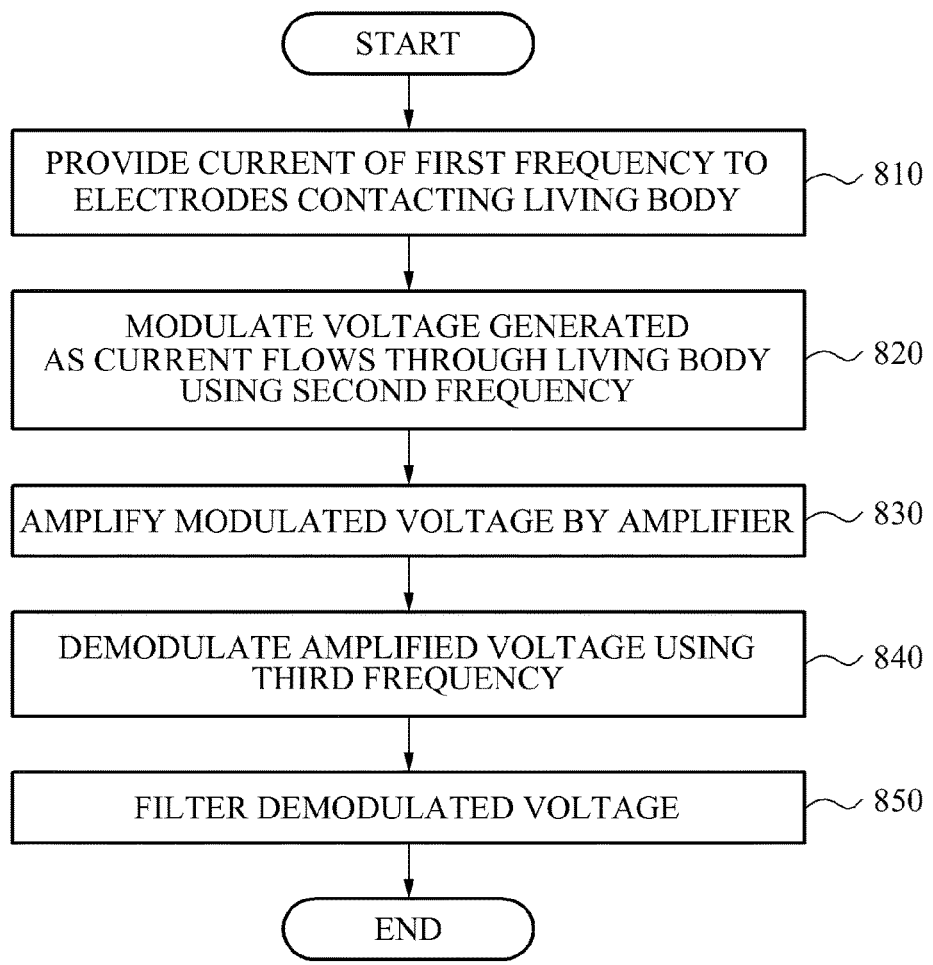
FIG. 8 is an operation flowchart illustrating an example of a bio impedance measurement method.

FIG. 8 is an operation flowchart illustrating an example of a bio impedance measurement method. Referring to FIG. 8, in operation 810, the bio impedance measurement method includes providing a current of a first frequency to electrodes contacting a living body. In operation 820, the bio impedance measurement method includes modulating a voltage generated as current flows through the living body, using a second frequency. In operation 830, the bio impedance measurement method includes amplifying the modulated voltage by an amplifier. In operation 840, the bio impedance measurement method includes demodulating the amplified voltage using a third frequency. In operation 850, the bio impedance measurement includes filtering the demodulated voltage, namely, canceling a signal of a higher frequency than the third frequency from a frequency band of the demodulated voltage. Since the technical features illustrated with reference to FIGS. 1A to 7B may be directly applied to the operations of FIG. 8, a detailed description will be omitted.

Figure 9:
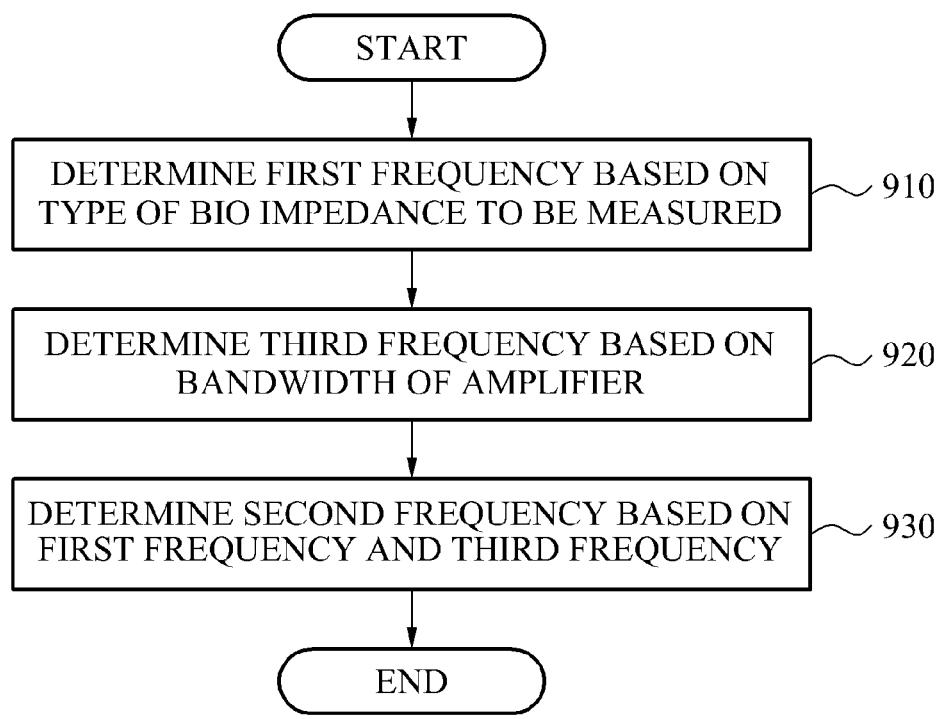
FIG. 9 is an operation flowchart illustrating an example of a method of determining frequencies.

FIG. 9 is an operation flowchart illustrating an example of a method of determining frequencies. Referring to FIG. 9, in operation 910, the method includes determining a first frequency based on a type of bio impedance to be measured. In operation 920, the method includes determining a third frequency based on a bandwidth of an amplifier. In operation 930, the method includes determining a second frequency based on the first frequency and the third frequency.

The method of determining the frequencies may be performed by the controller 160 of FIG. 4, the controller 510 of FIG. 5A, or the controller 510 of FIG. 5B. For example, the bandwidth of the amplifier may be about 10 kHz, and a frequency of an AC output from a current applicator may be about 100 kHz. The controller may determine the third frequency to be about 2 kHz so that the third frequency is fully included in the bandwidth of the amplifier. Furthermore, the controller may determine the second frequency by subtracting the third frequency from the first frequency. The second frequency may be determined as 100 kHz−2 kHz=98 kHz.

The various modules, elements, and methods described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A bio impedance measurement apparatus comprising:
   a current applicator configured to provide, to terminals contacting a body, a current based on a first control signal;
   a modulator configured to modulate a voltage generated as the current flows through the body, based on a second control signal;
   an amplifier configured to amplify the modulated voltage; and
   a demodulator configured to demodulate the amplified voltage based on a third control signal.

2. The bio impedance measurement apparatus of claim 1, wherein the third control signal has a third frequency that is a difference between a first frequency of the first control signal and a second frequency of the second control signal.

3. The bio impedance measurement apparatus of claim 1, wherein the third control signal has a third frequency that is determined based on a bandwidth of the amplifier.

4. The bio impedance measurement apparatus of claim 1, wherein the second control signal has a second frequency that is determined so that a frequency obtained by subtracting the second frequency from a first frequency of the first control signal is in a bandwidth of the amplifier.

5. The bio impedance measurement apparatus of claim 1, wherein the first control signal is determined based on a characteristic of a bio impedance to be measured.

6. The bio impedance measurement apparatus of claim 1, wherein the amplifier is configured to:
   amplify a signal generated based on the second control signal determined based on the first control signal and the third control signal.

7. The bio impedance measurement apparatus of claim 1, wherein:
   the modulator is configured to generate a first intermediate signal of a frequency obtained by adding a second frequency of the second control signal to a first frequency of the first control signal, and a second intermediate signal of a frequency obtained by subtracting the second frequency from the first frequency; and
   the amplifier configured to selectively amplify the second intermediate signal between the first intermediate signal and the second intermediate signal.

8. The bio impedance measurement apparatus of claim 1, further comprising:
   a selector configured to select the third control signal to be a fourth control signal or a fifth control signal, the fourth control signal and the fifth control signal having different phases.

9. The bio impedance measurement apparatus of claim 8, wherein the selector is configured to:
   select the fourth control signal to measure a real component of a bio impedance; and
   select the fifth control signal to measure an imaginary component of a bio impedance.

10. The bio impedance measurement apparatus of claim 8, wherein the selector is configured to:
    alternately select the fourth control signal and the fifth control signal at a predetermined period.

11. The bio impedance measurement apparatus of claim 1, further comprising:
    the terminals configured to contact the body so that the current flows through the body.

12. A bio impedance measurement method comprising:
    providing, to terminals contacting a body, a current based on a first control signal;

modulating a voltage generated as the current flows through the body, based on a second control signal;

amplifying the modulated voltage; and demodulating the amplified voltage based on a third control signal.

13. The bio impedance measurement method of claim 12, further comprising:

determining the first control signal based on a characteristic of a bio impedance to be measured;

determining the third control signal based on a bandwidth of an amplifier; and determining the second control signal based on the first control signal and the third control signal.

14. The bio impedance measurement method of claim 13, wherein the determining of the second control signal comprises:

determining a second frequency of the second control signal to be a difference between a first frequency of the first control signal and a third frequency of the third control signal.

15. The bio impedance measurement method of claim 13, wherein the determining of the third control signal comprises:

determining a third frequency of the third control signal so that the third frequency is in the bandwidth of the amplifier.

16. The bio impedance measurement method of claim 12, wherein:

the modulating comprises generating a first intermediate signal of a frequency obtained by adding a second frequency of the second control signal to a first frequency of the first control signal, and a second intermediate signal of a frequency obtained by subtracting the second frequency from the first frequency; and the amplifying comprises selectively amplifying the second intermediate signal between the first intermediate signal and the second intermediate signal.

17. The bio impedance measurement method of claim 12, wherein the demodulating comprises:

selecting the third control signal to be a fourth control signal or a fifth control signal, the fourth control signal and the fifth control signal having different phases.

18. The bio impedance measurement method of claim 17, wherein the selecting comprises:

selecting the fourth control signal to measure a real component of a bio impedance; and selecting the fifth control signal to measure an imaginary component of a bio impedance.

19. The bio impedance measurement method of claim 17, wherein the selecting comprises:

alternately selecting the fourth control signal and the fifth control signal at a predetermined period.

20. A non-transitory computer-readable storage medium storing a program comprising instructions to cause a computer to perform the method of claim 12.

* * * * *